US008722331B2

(12) United States Patent
Demuth et al.

(10) Patent No.: US 8,722,331 B2
(45) Date of Patent: May 13, 2014

(54) METHOD FOR SELECTING A TREATMENT FOR NON-SMALL CELL LUNG CANCER USING GENE EXPRESSION PROFILES

(75) Inventors: Jeffrey P. Demuth, Blanchester, OH (US); Erin L. Crawford, Rossford, OH (US); James C. Willey, Toledo, OH (US); David A. Weaver, Perrysburg, OH (US); Kristy A. Warner, Deerfield, MI (US); Timothy G. Graves, Toledo, OH (US)

(73) Assignee: University of Toledo, Toledo, OH (US)

( * ) Notice: Subject to any disclaimer, the term of this patent is extended or adjusted under 35 U.S.C. 154(b) by 1019 days.

(21) Appl. No.: 10/508,932

(22) PCT Filed: Mar. 27, 2003

(86) PCT No.: PCT/US03/09428
§ 371 (c)(1),
(2), (4) Date: Sep. 24, 2004

(87) PCT Pub. No.: WO03/082078
PCT Pub. Date: Oct. 9, 2003

(65) Prior Publication Data
US 2005/0260586 A1 Nov. 24, 2005

Related U.S. Application Data

(60) Provisional application No. 60/368,288, filed on Mar. 28, 2002, provisional application No. 60/368,409, filed on Mar. 28, 2002.

(51) Int. Cl.
C12Q 1/68 (2006.01)
(52) U.S. Cl.
CPC ............ *C12Q 1/6851* (2013.01); *C12Q 1/6886* (2013.01); *C12Q 2600/106* (2013.01); *C12Q 2600/158* (2013.01); *C12Q 2600/112* (2013.01); *C12Q 2600/16* (2013.01); *C12Q 2565/501* (2013.01)
USPC ........ 435/6.11; 435/6.12; 435/6.14; 435/6.18

(58) Field of Classification Search
CPC ............... C12Q 1/6851; C12Q 1/6886; C12Q 2600/106; C12Q 2600/158; C12Q 2600/16; C12Q 2600/112; C12Q 2565/1501
See application file for complete search history.

(56) References Cited

U.S. PATENT DOCUMENTS

| | | |
|---|---|---|
| 5,639,606 A | 6/1997 | Willey |
| 5,643,765 A | 7/1997 | Willey |
| 5,789,167 A | 8/1998 | Konrad |
| 5,866,617 A | 2/1999 | Hausheer et al. |
| 5,876,978 A | 3/1999 | Willey |
| 6,001,817 A | 12/1999 | Shaw |
| 6,001,991 A | 12/1999 | Dean |
| 6,080,727 A | 6/2000 | Zupi |
| 6,218,122 B1 | 4/2001 | Friend |
| 6,229,911 B1 | 5/2001 | Balaban et al. |
| 6,316,272 B1 | 11/2001 | Mack |
| 2003/0186246 A1 | 10/2003 | Willey et al. |
| 2007/0092892 A1 | 4/2007 | Willey et al. |

FOREIGN PATENT DOCUMENTS

WO   WO 99/01581 A1   1/1999

OTHER PUBLICATIONS

Damia et al. European Journal of Cancer. 1998. 34: 1783-1788.*
Young et al. Clinical Cancer Research. Mar. 1999. 5: 673-680.*
Kool et al. Cancer Research. 1997. 57: 3537-3547.*
Oguri et al. International Journal of Cancer. 2000. 86: 95-100.*
Steinbach et al. Clinical Cancer Research. 2003. 9: 1083-1086.*
Bhattacharjee et al. PNAS. 2001. 98: 13790-13795.*
James C. Willey, Erin L. Crawford, Clara M. Jackson, David A. Weaver, Jeremy C. Hoban, Sadik A. Khuder and Jeffrey P. Demuth—Expression Measurement of Many Genes Simultaneously by Quantitative RT-PCR Using Standardized Mixtures of Competitive Templates—Rapid Communication—Published 1998—A merican Journal of Respiratory Cell and Molecular Biology—vol. 19—12 pages—US.
Jeffrey P. Demuth, Clara M. Jackson, David A. Weaver, Erin L. Crawford, Dennis S. Durzinsky, Samuel J. Durham, Aiman Zaher, Edwin R. Phillips, Sadik A. Khuder and James C. Willey—The Gene Expression Index c-myc X E2F-1/p21 is Highly Predictive of Malignant Phenotype in Human Bronchial Epithelial Cells—Rapid Communication—Published 1998—7 pages—American Journal of Respiratory Cell and Molecular Biology vol. 19—US.
Jeffrey K. Actor, Josef R. Limor and Robert L. Hunter—A Flexible Bioluminescent-Quantitative Polymerase Chain Reaction Assay for Analysis of Competitive PCR Amplicons—Journal of Clinical Laboratory Analysis—Published 1999—8 pages—US.
B. W. S. Robinson, D.J. Erle, D.A. Jones, S. Shapiro, W. J. Metzger, S. M. Albelda, W.C. Parks and A. Boylan—Recent advance in molecular biological techniques and their relevance to pulmonary research—Occasional review—Pu blished 2000—11 pages—US.
EP International Search Report—Feb. 11, 2005.
Alizadeh, A.A., et al. 2000. Distinct types of diffuse large B-cell lymphoma identified by gene expression profiling. *Nature.* 403(6769): 503-511.
Apostolakos, M.J., et al. 1993. Measurement of gene expression by multiplex competitive polymerase chain reaction. *Anal. Biochem.* 213: 277-284.
Crawford, E.L., et al. 2000. Normal bronchial epithelial cell expression of glutathione transferase P1, glutathione transferase M3, and glutathione peroxidase is low in subjects with bronchogenic carcinoma. *Cancer Res.* 60: 1609-1618.

(Continued)

*Primary Examiner* — Carla Myers
(74) *Attorney, Agent, or Firm* — MacMillan, Sobanski & Todd, LLC

(57) ABSTRACT

The present invention identifies and quantifies changes in gene expression associated with non-small cell lung cancer NSCLC by examining gene expression in tissue from normal lung and diseased lung. The present invention also identifies and quantifies expression profiles which serve as useful diagnostic markers as well as markers that are useful to monitor disease states, disease progression, drug toxicity, drug efficacy and drug metabolism.

5 Claims, 10 Drawing Sheets

(56) References Cited

OTHER PUBLICATIONS

Crawford, E.L., et al. 2002. Multiplex standardized RT-PCR for expression analysis of many genes in small clinical samples. *Biochemical and Biophysical Research Communications*. 293: 509-516.

Golub, T.R., et al. 1999. Molecular classification of cancer: class discovery and class prediction by gene expression monitoring. *Science*. 286. 531-537.

Kihara, C., et al. 2001. Prediction of sensitivity of esophageal tumors to adjuvant chemotherapy by cDNA microarray analysis of gene-expression profiles. *Cancer Res*. 61: 6474-6479.

Prakash, S., et al. 1993. DNA repair genes and proteins of *Saccharoyces cerevisiae*. *Anna. Rev. Genet*. 27: 33-70.

Scherf, U., et al. 2000. A gene expression database for the molecular pharmacology of cancer. *Nat Genet*. 24: 236-244.

Weaver, et al. 2001. Comparison of expression patterns by microarray and standardized RT-PCR analyses in lung cancer cell lines with varied sensitivity to carboplatin. *Proc. Am. Assoc. Cancer Res*. 42: 606.

Willey, J.C., et al. 1997. Quantitative RT-PCR measurement of cytochromes p4a50 1A1, 1B1, and 2B7, microsomal epoxide hydrolase, and NADPH oxidereductase expression in lung cells of smokers and non-smokers. *Am. J. Respir. Cell Mol. Biol.* 17: 114-124.

Zembutsu, H., et al. 2002. Genome-wide cDNA microarray screening to correlate gene expression profiles with sensitivity of 85 human cancer xenografts to anticancer drugs. *Cancer Res*. 62: 518-527.

Peters, Nils et al. 1999. Quantitative analysis of NF1 and OMGP gene transcripts in sporadic gliomas, sporadic meningiomas and neurofibromatosis type 1-associated plexiform neurofibromas. *Acta Neuropathologica*. 97 (6): 547-551. (Abstract Only).

Spanakis, Emmanuel. 1993. Problems related to the interpretation of autoradiographic data on gene expression using common constitutive transcripts as controls. *Nucleic Acids Research*. 21 (16): 3809-3819. (Abstract Only).

Weaver, et al. ABCC5, ERCC2, XPA and XRCC1 transcript abundance levels correlate with cisplatin chemoresistance in non-small cell lung cancer cell lines. Mol Cancer. May 9, 2005;4(1):18 (8 pages).

\* cited by examiner

| Gene | GenBank accesion No. | Seq. ID No. | Primer | Sequence | bp postion in cDNA | length (bp) |
|---|---|---|---|---|---|---|
| ACTB | X00351 | 1 | Forward | 5' GAT TCC TAT GTG GGC GAC GAG 3' | 192-212 | 532 |
|  |  | 2 | Reverse | 5' CCA TCT CTT GCT CGA AGT CC 3' | 704-723 | 416 |
|  |  | 3 | CT | 5' CCA TCT CTT GCT CGA AGT CCG CCA GCC AGG TCC AGA CGC A 3' | 568-587 |  |
| ABCC1 | L05628 | 4 | Forward | 5' CAC CTG AAG GAC TTC GTG TCA G 3' | 4415-4436 | 460 |
|  |  | 5 | Reverse | 5' TGG TTT ACC AGG GGT ACT GAC T 3' | 4853-4874 | 381 |
|  |  | 6 | CT | 5' TGG TTT ACC AGG GGT ACT GAC TTT GGC CAT GCT GTA GAA AAG AC 3' | 4752-4773 |  |
| ABCC4 | AF071202 | 7 | Forward | 5' GAA GCA CCT TGG GAA TAT CAG AAA 3' | 3179-3202 | 497 |
|  |  | 8 | Reverse | 5' AGG CAC ACC AGT TGT CTT TGT CCA 3' | 3652-3675 | 421 |
|  |  | 9 | CT | 5' AGG CAC ACC AGT TGT CTT TGT CCA GTA CCT CTT GTA AGG CAT TCC ACA 3' | 3552-3575 |  |
| ABCC5 | U83661 | 10 | Forward | 5' CAT CTC TTA TGC TGT CCA GTT AAC 3' | 3515-3538 | 434 |
|  |  | 11 | Reverse | 5' GCT CTT GAG GAA TGA TAG AGA GTT 3' | 3925-3948 | 346 |
|  |  | 12 | CT | 5' GCT CTT GAG GAA TGA TAG AGA GTT GGC CAT CCC CAG CGA GGA CTT CC 3' | 3814-3837 |  |
| ABCC10 | U66684 | 13 | Forward | 5' GGA ATN GGT GAA CTG GGT GAA G 3' | 1197-1218 | 521 |
|  |  | 14 | Reverse | 5' CAA GGA GTG ATT TCC AAA GAG T 3' | 1696-1717 | 452 |
|  |  | 15 | CT | 5' CAA GGA GTG ATT TCC AAA GAG TCA GCC AGC ACC TCT GTA TAG GC 3' | 1605-1626 |  |
| DDIT3 | S40706 | 16 | Forward | 5' AGA ATC AAA AAT CTT CAC CAC T 3' | 312-333 | 515 |
|  |  | 17 | Reverse | 5' CTT TCC TTT TGT CTA CTC CAA G 3' | 805-826 | 457 |
|  |  | 18 | CT | 5' CTT TCC TTT TGT CTA CTC CAA GTC AGT AGC CAC TTC TGG GAA AG 3' | 725-746 |  |
| ERCC2 | X52221/X52470 | 19 | Forward | 5' GGC CTT CTT CAC CAG CTA C 3' | 2289-2307 | 415 |
|  |  | 20 | Reverse | 5' GTA GTC CGT CTT GCC CCT G 3' | 2685-2703 | 346 |
|  |  | 21 | CT | 5' GTA GTC CGT CTT GCC CCT GTG GAA CTG GTC CCG CAG GT 3' | 2597-2615 |  |

Fig. 1a- Table 1

| Gene | Accession | SEQ ID | Direction | Sequence | Position | Length |
|---|---|---|---|---|---|---|
| ERCC3 | M31899 | 22 | Forward | 5' TCG GGG GTC ATT GTT CTT CC 3' | 1098-1117 | |
| | | 23 | Reverse | 5' TCT TGG CTG GTA TGG TGT GC 3' | 1424-1443 | 346 |
| | | 24 | CT | 5' TCT TGG CTG GTA TGG TGT GCA GGT GCT AAT GGC AAC GGA G 3' | 1304-1323 | 246 |
| GTF2H2 | AF078847 | 25 | Forward | 5' CTC TTT CAG CAT GGC GCA TTT GGA TGG C 3' | 1002-1029 | |
| | | 26 | Reverse | 5' CTT TCA ATT CCC CCT GAC ATC CAT AAC A 3' | 1228-1255 | 254 |
| | | 27 | CT | 5' CTT TCA ATT CCC CCT GAC ATC CAT AAC AGC AGA CAC CAA AGT AAG ACC AC 3' | 1118-1145 | 166 |
| LIG1 | M36067 | 28 | Forward | 5' CAT GAT CCT GAA GCA GAC GT 3' | 1620-1639 | |
| | | 29 | Reverse | 5' GTG TCC AGG ATG AAG GAT GT 3' | 1960-1979 | 360 |
| | | 30 | CT | 5' GTG TCC AGG ATG AAG GAT GTC AGT GTT GTC TTC CTG ATT C 3' | 1887-1906 | 307 |
| XPA | D14533 | 31 | Forward | 5' CTC GGC GAC GGC TGC GGC TAC TGG AG 3' | 170-198 | |
| | | 32 | Reverse | 5' TGT CGG ACT TCC TTT GCT TCT TCT AAT GC 3' | 621-649 | 480 |
| | | 33 | CT | 5' TGT CGG ACT TCC TTT GCT TCT TCT AAT GCT CTT CTT CAC AAT AAA TTT AAG AG 3' | 508-536 | 391 |
| XPC | D21089 | 34 | Forward | 5' GGC TAC TCC CAT CCC GTG ACT 3' | 2509-2529 | |
| | | 35 | Reverse | 5' TTT CCC TTT TGG TCT TCT TGG 3' | 2864-2884 | 376 |
| | | 36 | CT | 5' TTT CCC TTT TGG TCT TCT TGG TCC CCT CTT CAT CAG AAG 3' | 2753-2773 | 286 |
| XRCC1 | M36089 | 37 | Forward | 5' CCC CTG AAG AGA CCA AAG CA 3' | 1906-1925 | |
| | | 38 | Reverse | 5' CCA TTG AAG GCT GTG ACG TA 3' | 2241-2260 | 355 |
| | | 39 | CT | 5' CCA TTG AAG GCT GTG ACG TAT CAG GGA CTG GCA GAT CAG G 3' | 2142-2161 | 276 |

Fig. 1b- Table 1 (cont.)

Fig. 2 – Table 2

|  | NSCLC cell line | Cisplatin |
|---|---|---|
| Group 1[b] | NCI-H460 | 0.52 ± 0.04 |
|  | NCI-H1155 | 0.90 ± 0.20 |
|  | NCI-H23 | 2.09 ± 0.32 |
|  | NCI-H838 | 3.86 ± 0.31 |
|  | NCI-H1334 | 5.15 ± 0.47 |
|  | NCI-H1437 | 5.90 ± 1.61 |
|  | NCI-H1355 | 6.74 ± 1.29 |
|  | NCI-H1435 | 22.86 ± 2.36 |
| Group 2[c] | NCI-H358 | 1.16 ± 0.24 |
|  | NCI-H322 | 2.85 ± 0.22 |
|  | NCI-H441 | 3.38 ± 0.99 |
|  | NCI-H522 | 3.53 ± 0.56 |
|  | NCI-H226 | 5.05 ± 0.95 |
|  | NCI-H647 | 7.27 ± 1.14 |

[a] Previously published results by Chun-Ming Tsai, et.al. (21)
[b] Initial set of 8 NSCLC cell lines evaluated.
[c] Additional set of 6 NSCLC cell lines evaluated.

| NSCLC cell line | | LIG1 | ERCC2 | ERCC3 | DDIT3 | ABCC1 | ABCC4 |
|---|---|---|---|---|---|---|---|
| NCI-H460 | Mean | 3.53E+02 | 2.54E+02 | 3.07E+02 | 1.00E+02 | 7.37E+02 | 3.50E+02 |
| | S or R[a] | 2.12E+01 S | 2.11E+01 S | 1.18E+02 S | 5.26E+01 S | 2.75E+02 S | 2.19E+02 S |
| NCI-H1155 | Mean | 5.90E+02 | 5.81E+02 | 1.27E+03 | 1.26E+03 | 3.84E+02 | 3.30E+02 |
| | S or R | 7.40E+01 R | 7.90E+01 R | 4.70E+02 R | 9.00E+01 R | 1.85E+02 R | 1.43E+02 R |
| NCI-H23 | Mean | 7.74E+02 | 8.29E+02 | 1.81E+03 | 1.55E+03 | 3.13E+02 | 1.87E+03 |
| | S or R | 2.85E+02 S | 5.46E+02 S | 2.47E+02 S | 3.03E+02 S | 9.75E+01 S | 3.80E+02 S |
| NCI-H838 | Mean | 1.16E+03 | 8.69E+03 | 1.81E+03 | 5.79E+02 | 6.21E+03 | 1.35E+03 |
| | S or R | 5.32E+02 S | 8.37E+03 R | 1.35E+03 R | 6.80E+02 R | 3.90E+03 R | 1.26E+03 R |
| NCI-H1334 | Mean | 4.50E+02 | 1.28E+03 | 7.66E+02 | 6.17E+02 | 5.48E+02 | 6.05E+02 |
| | S or R | 2.59E+02 S | 2.12E+02 S | 1.65E+02 S | 1.52E+02 S | 2.50E+02 S | 1.12E+02 S |
| NCI-H1437 | Mean | 2.56E+02 | 6.13E+02 | 3.72E+02 | 4.59E+02 | 8.48E+02 | 4.05E+01 |
| | S or R | 1.42E+02 S | 1.49E+02 S | 7.62E+01 S | 2.87E+02 S | 2.71E+02 S | 3.37E+01 S |
| NCI-H1355 | Mean | 9.03E+02 | 6.52E+02 | 1.01E+03 | 3.75E+02 | 1.48E+03 | 1.10E+03 |
| | S or R | 4.45E+02 S | 2.57E+02 S | 3.36E+02 S | 2.49E+02 S | 4.72E+02 S | 1.80E+02 S |
| NCI-H1435 | Mean | 2.59E+03 | 3.01E+04 | 3.37E+03 | 3.76E+03 | 9.24E+03 | 2.24E+03 |
| | S or R | 7.47E+02 S | 8.82E+03 S | 1.14E+03 S | 1.40E+03 S | 3.71E+03 S | 8.75E+02 S |
| NCI-H358 | Mean | | 1.32E+03 | | | | |
| | S or R | | 4.40E+02 S | | | | |
| NCI-H322 | Mean | | 4.02E+03 | | | | |
| | S or R | | 1.58E+03 S | | | | |
| NCI-H441 | Mean | | 1.19E+03 | | | | |
| | S or R | | 2.52E+02 S | | | | |
| NCI-H522 | Mean | | 7.12E+02 | | | | |
| | S or R | | 1.62E+02 S | | | | |
| NCI-H226 | Mean | | 8.85E+02 | | | | |
| | S or R | | 2.74E+02 S | | | | |
| NCI-H647 | Mean | | 4.64E+03 | | | | |
| | S or R | | 2.84E+03 S | | | | |

Fig. 3a – Table 3

| NSCLC cell line | | ABCC5 | ABCC10 | GTF2H2 | XPA | XPC | XRCC1 |
|---|---|---|---|---|---|---|---|
| NCI-H460 | Mean | 5.93E+01 | 1.80E+01 | 1.02E+03 | 3.10E+02 | 5.25E+02 | 1.88E+03 |
|  | S or R[a] | 2.61E+01 S | 2.65E+00 S | 3.58E+02 S | 2.53E+02 S | 1.74E+02 S | 7.60E+02 S |
| NCI-H1155 | Mean | 8.97E+01 | 4.25E+01 | 1.09E+03 | 1.65E+03 | 2.33E+03 | 4.04E+03 |
|  | S or R | 3.23E+01 S | 3.70E+01 R | 7.47E+02 R | 1.75E+03 R | 6.50E+02 R | 1.60E+02 R |
| NCI-H23 | Mean | 1.39E+02 | 4.56E+02 | 4.42E+03 | 1.18E+03 | 1.44E+03 | 8.27E+03 |
|  | S or R | 1.50E+01 S | 2.62E+02 S | 3.24E+03 S | 2.53E+02 S | 7.98E+02 S | 6.52E+03 S |
| NCI-H838 | Mean | 4.01E+02 | 5.12E+02 | 4.18E+03 | 2.23E+03 | 5.35E+03 | 3.14E+04 |
|  | S or R | 5.90E+01 R | 3.30E+02 R | 2.73E+03 R | 2.16E+03 R | 6.05E+03 R | 3.75E+04 R |
| NCI-H1334 | Mean | 9.90E+01 | 1.17E+02 | 1.33E+03 | 5.07E+02 | 1.18E+03 | 6.53E+03 |
|  | S or R | 4.51E+01 S | 6.17E+01 S | 4.46E+02 S | 3.91E+02 S | 1.50E+02 S | 1.93E+03 S |
| NCI-H1437 | Mean | 2.64E+02 | 2.00E+02 | 1.74E+03 | 5.84E+02 | 7.30E+02 | 2.84E+03 |
|  | S or R | 2.02E+02 S | 2.08E+02 S | 5.20E+02 S | 2.98E+02 S | 5.79E+02 S | 6.49E+02 S |
| NCI-H1355 | Mean | 2.67E+02 | 8.28E+01 | 1.04E+03 | 1.34E+03 | 1.37E+03 | 4.57E+03 |
|  | S or R | 2.47E+02 S | 4.12E+01 S | 4.73E+02 S | 5.10E+02 S | 7.70E+02 S | 7.38E+02 S |
| NCI-H1435 | Mean | 1.39E+03 | 3.31E+02 | 2.84E+03 | 6.77E+03 | 1.93E+03 | 4.19E+04 |
|  | S or R | 6.10E+02 S | 8.14E+01 S | 3.84E+02 S | 1.79E+03 S | 5.38E+02 S | 2.87E+03 S |
| NCI-H358 | Mean | 6.80E+01 |  | 1.02E+03 | 1.34E+03 | 1.03E+03 | 4.02E+03 |
|  | S or R | 3.10E+01 S |  | 6.73E+02 S | 6.63E+02 S | 3.18E+02 S | 1.72E+03 S |
| NCI-H322 | Mean | 4.50E+01 |  | 6.63E+02 | 6.64E+02 | 5.51E+02 | 3.87E+03 |
|  | S or R | 8.00E+00 S |  | 1.22E+02 S | 3.42E+02 S | 3.14E+02 S | 7.91E+02 S |
| NCI-H441 | Mean | 1.57E+02 |  | 1.14E+03 | 6.11E+02 | 7.28E+02 | 2.96E+03 |
|  | S or R | 5.50E+01 S |  | 3.23E+02 S | 1.32E+02 S | 1.46E+02 S | 6.11E+02 S |
| NCI-H522 | Mean | 4.03E+02 |  | 2.46E+03 | 4.83E+02 | 4.54E+02 | 2.41E+03 |
|  | S or R | 4.00E+01 S |  | 1.43E+03 S | 2.68E+02 S | 3.00E+01 S | 5.82E+02 S |
| NCI-H226 | Mean | 1.04E+02 |  | 1.10E+03 | 5.97E+02 | 3.52E+03 | 2.46E+03 |
|  | S or R | 1.60E+01 S |  | 3.85E+02 S | 1.17E+02 S | 1.31E+03 S | 7.94E+02 S |
| NCI-H647 | Mean | 1.92E+02 |  | 8.84E+02 | 1.06E+03 | 2.71E+03 | 1.04E+04 |
|  | S or R | 3.90E+01 S |  | 1.22E+02 S | 4.90E+02 S | 8.06E+02 S | 4.94E+03 S |

Fig. 3b – Table 3 (cont.)

|  | Group 1[a] | | Groups 1 and 2[b] | |
| --- | --- | --- | --- | --- |
| Gene | $R^2$ | p value | $R^2$ | p value |
| ABCC5 | 0.93 | 0.0001 | 0.85 | 0.0001 |
| ERCC2 | 0.85 | 0.0012 | 0.82 | 0.0001 |
| XPA | 0.81 | 0.0023 | 0.75 | 0.0001 |
| LIG1 | 0.78 | 0.0034 | Na[c] | |
| DDIT3 | 0.68 | 0.0120 | NA | |
| ABCC1 | 0.64 | 0.0164 | NA | |
| XRCC1 | 0.56 | 0.0318 | 0.57 | 0.0019 |
| ERCC3 | 0.56 | 0.0319 | NA | |
| ABCC4 | 0.37 | 0.1081 | NA | |
| ABCC10 | 0.06 | 0.5641 | NA | |
| GTF2H2 | 0.02 | 0.7424 | 0.04 | 0.5183 |
| XPC | 0.00 | 0.9851 | 0.02 | 0.6654 |

[a] Initial 8 NSCLC cell lines analyzed as reported in Table 2.
[b] All 14 NSCLC cell lines analyzed as reported in Table 2.
[c] Not assessed.

Fig. 4 - Table 4

| Model | Group 1[b] | | Groups 1 and 2[c] | |
| --- | --- | --- | --- | --- |
| Single variable | Model $R^2$ | p value[d] | Model $R^2$ | p value |
| ERCC2/XPC | 0.91 | 0.0002 | 0.69 | 0.0002 |
| ABCC5/GTF2H2 | 0.91 | 0.0002 | 0.88 | 0.0001 |
| ERCC2/XRCC1 | 0.90 | 0.0003 | NS[e] | |
| ERCC2/GTF2H2 | 0.90 | 0.0004 | 0.63 | 0.0007 |
| XPA/XPC | 0.89 | 0.0004 | 0.62 | 0.0008 |
| XRCC1/XPC | 0.88 | 0.0005 | 0.75 | 0.0001 |
| ABCC5/XPC | 0.88 | 0.0006 | 0.29 | 0.0461 |
| Two variable | Model $R^2$ | p value | Model $R^2$ | p value |
| ABCC5/GTF2H2 and ERCC2/GTF2H2 | 0.96 | 0.0003 | 0.91 | 0.0001 |

[a] SAS version 6, 4th edition, volume 2.
[b] 8 NSCLC cell lines analyzed as reported in Table 2.
[c] 14 NSCLC cell lines analyzed as reported in Table 2.
[d] p value is shown for each ratio in the model.
[e] not significant (p > 0.05).

Fig. 5 – Table 5

Effect of Collection Methods on RNA Quality in H1155 Human NSCLC Cells

| Collection agent | 1 day RNA | 3 day RNA | actin | 10 day RNA | actin | 30 day RNA | actin |
|---|---|---|---|---|---|---|---|
| Preservcyt-4 | [a]++ | ++ | [b]+NT | ++ | +NT | ++ | +NT |
| Preservcyt-20 | ++ | ++ | +NT | ++ | +NT | ++ | +NT |
| | | | | | | | |
| RNA Later-4 | ++ | ++ | +NT | ++ | +NT | + | +NT |
| RNA Later-20 | ++ | ++ | +NT | ++ | +NT | - | [c]-NT |
| | | | | | | | |
| Tri-reagent-4 | ++ | ++ | +NT | ++ | +NT | ++ | +NT |
| Tri-reagent-20 | ++ | ++ | +NT | ++ | +NT | ++ | +NT |

[a] ++ = 2 ribosomal peaks; [b] +NT = native actin; [c] –NT + no native actin

Fig. 6 – Table 6

Cytological Information and Diagnosis of FNA specimens

| FNA Sample | Cellularity | % Tumor | Viability | FNA Diagnosis | Final Diagnosis | RNA Quality | β-actin |
|---|---|---|---|---|---|---|---|
| 110 | L | 90 | H | NSCLC | Squamous | +- | + |
| 123 | L | 90 | L | NSCLC | Squamous | ++ | + |
| 125 | H | 90 | H | NSCLC | NSCLC | ++ | + |
| 135 | L | 70 | L | NSCLC | NSCLC | - | - |
| 138 | H | 90 | L | NSCLC | NSCLC | NE | + |
| 148a | L | 80 | L | Atypical | SCLC | ++ | + |
| 148b | L | 60 | L | Atypical | SCLC | - | + |
| 165 | L | 20 | L | Atypical | SCLC | +- | + |
| 171 | L | 10 | L | NSCLC | NSCLC | - | - |
| 172 | L | 20 | L | NSCLC | NSCLC | - | + |

Fig. 7 – Table 7

| Sample | | c-myc | E2F-1 | p21 | Index |
|---|---|---|---|---|---|
| 110 | Mean | 2.51E+05 | 4.85E+03 | 1.13E+05 | 1.00E+04 |
| | S.D. | 3.80E+05 | 4.60E+03 | 3.90E+04 | |
| 123 | Mean | 3.25E+05 | 5.49E+04 | 9.00E+04 | 2.00E+05 |
| | S.D. | 4.50E+04 | 2.30E+04 | 4.10E+04 | |
| 125 | Mean | 1.24E+05 | 4.08E+04 | 1.13E+05 | 4.50E+04 |
| | S.D. | 1.30E+05 | 1.80E+04 | 3.20E+04 | |
| 138 | Mean | 8.69E+04 | 2.30E+04 | 2.08E+04 | 9.70E+04 |
| | S.D. | 4.10E+04 | 3.40E+03 | 6.90E+03 | |
| 148a | Mean | 1.87E+03 | 1.82E+05 | 4.84E+04 | 7.00E+03 |
| | S.D. | 1.10E+03 | 2.50E+04 | 2.50E+04 | |
| 148b | Mean | 1.32E+03 | 3.48E+06 | 7.32E+04 | 6.30E+04 |
| | S.D. | 2.00E+02 | 4.70E+05 | 1.10E+04 | |
| 165 | Mean | 1.64E+04 | 3.59E+04 | 8.98E+03 | 2.00E+04 |
| | S.D. | 6.50E+03 | 1.90E+04 | 9.50E+02 | |
| 172 | Mean | 2.88E+06 | 1.72E+05 | 1.44E+05 | 3.40E+06 |
| | S.D. | 7.50E+05 | 3.30E+04 | 1.20E+05 | |

Gene Expression Values and Index Value for c-myc, E2F-1 and p21 in FNA samples

*No data obtained for sample 135 and 171.

Fig. 8 – Table 8

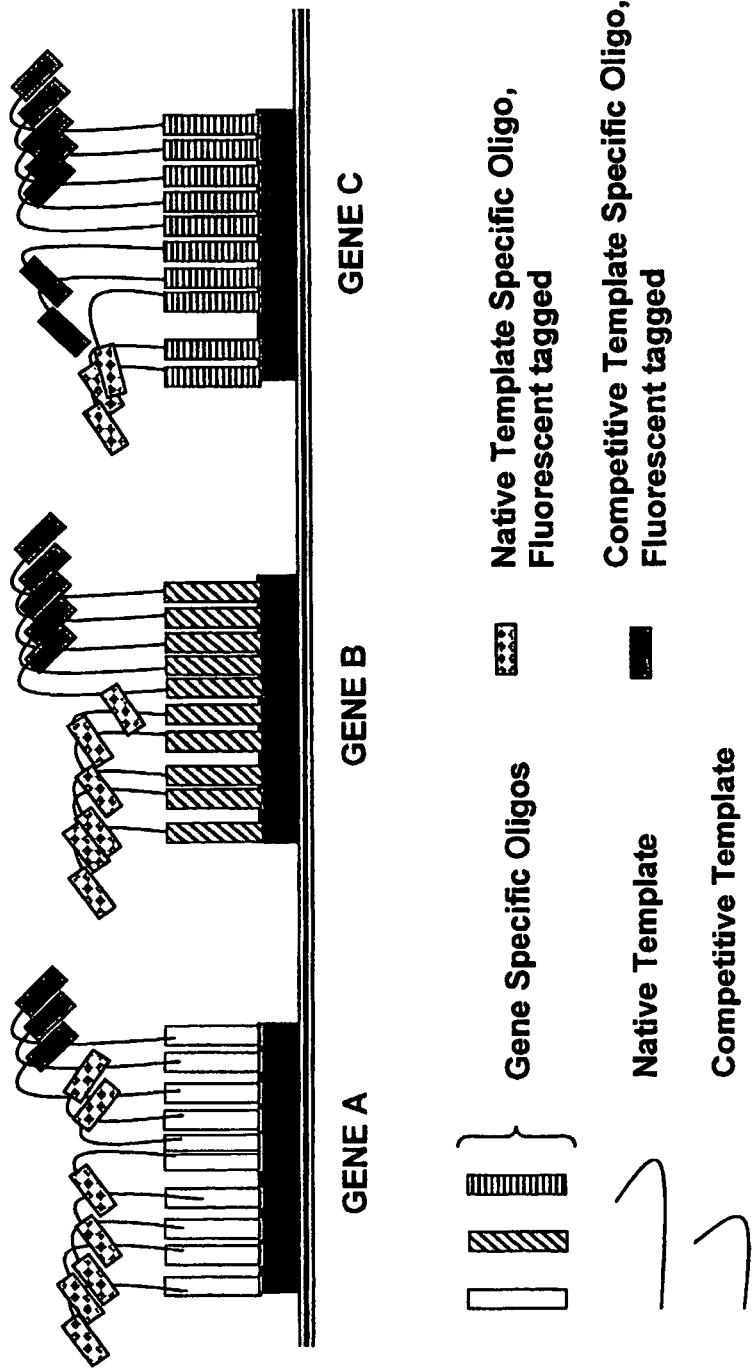

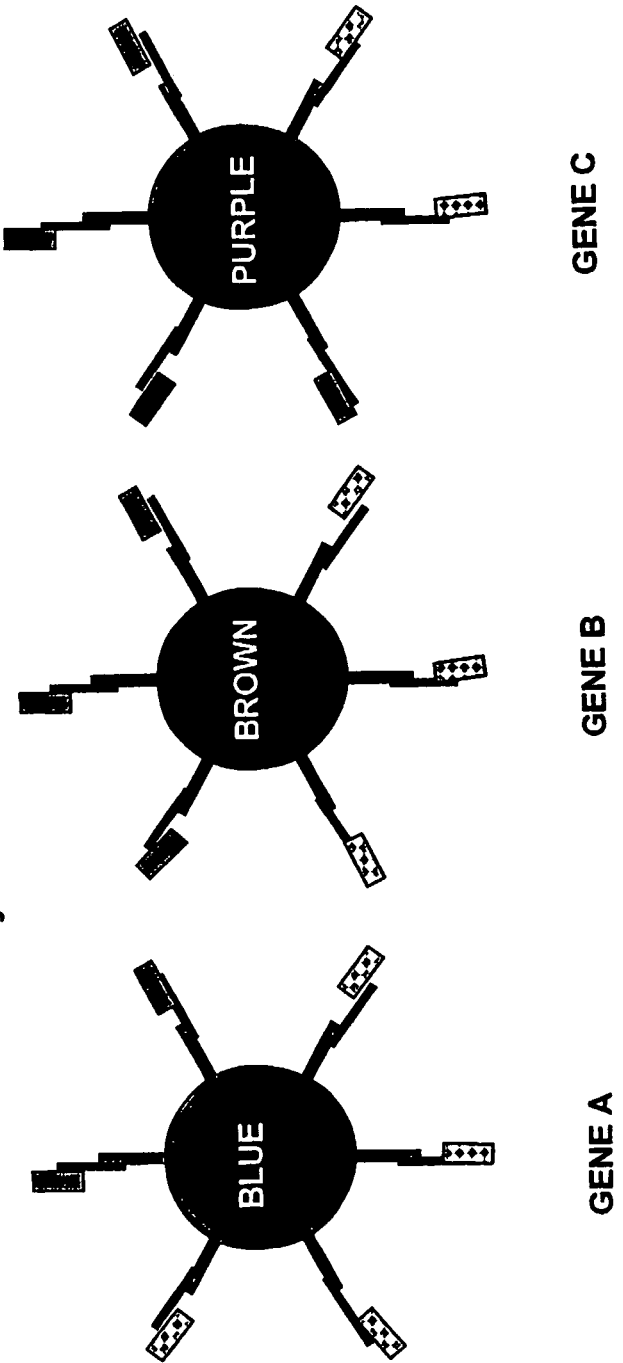
Fig. 9b MICROBEADS (Identity of gene known by fluorescent color of bead)

METHOD FOR SELECTING A TREATMENT FOR NON-SMALL CELL LUNG CANCER USING GENE EXPRESSION PROFILES

RELATED APPLICATION

The present application claims priority to U.S. Provisional Patent Application Ser. No. 60/368,288 filed on Mar. 28, 2002 and Ser. No. 60/368,409 filed on Mar. 28, 2002, which are expressly incorporated herein by reference in their entireties.

This invention was made under Research Grant Nos. NIH CA85147 and 81126 who may have certain rights thereto.

BACKGROUND OF THE INVENTION

Non-small cell lung cancer (NSCLC) is the most common type of bronchogenic carcinoma. Although chemotherapeutic regimens with greater efficacy continue to be developed, the best regimens presently give an overall regression rate of only 30-50%. This lack of response is attributable to resistance that is present de novo or develops in response to treatment. It is believed that mechanisms of chemoresistance likely involve multiple gene products. It is important to define the role of specific genes involved in tumor development and growth and to identify and quantify those genes and gene products that can serve as targets for diagnosis, prevention, monitoring and treatment of cancer.

In certain instances, therapeutic agents that are initially effective become ineffective or less effective for a patient over time. The same therapeutic agent can continue to be effective for a longer period of time for a different patient. Further, the therapeutic agents can be ineffective or harmful to still other patients. Therefore, it would be beneficial to identify genes and/or gene products that could serve as markers with respect to cancers and to given therapeutic agents. The ability to make such predictions and corrections in the treatment make it possible to more accurately make decisions on the therapeutic regime at an earlier stage in time in the course of a treatment of a patient.

Currently, cisplatin and carboplatin are among the most widely used cytotoxic anticancer drugs. However, resistance to these drugs through de novo or induced mechanisms undermines their curative potential. Perez, R. P., Cellular and molecular determinants of cisplatin resistance, Eur. J. Cancer (1998), 34, 1535-1542. Recently, understanding regarding potential modes of chemoresistance to platinum compounds has been obtained through studies correlating cytotoxicity with nucleotide excision-repair (NER) (Dijt, F., Fitchinger-Schepman, A. M., Berends, F., Reedikj, J., Formation and repair of cisplatin-induced adducts to DNA in cultured normal and repair-deficient human fibroblasts, Cancer Res. (1988), 48, 6058-6062. Zamble, D. B., Lippard, S. J., Cisplatin and DNA repair in cancer chemotherapy, Trends Biochem Sci (1995), 20, 435-439. States, J. C., Reed, E., Enhanced XPA mRNA levels in cisplatin-resistant human ovarian cancer are not associated with XPA mutations or gene amplifications, Cancer Lett. (1996), 108, 233-237. Ferry, K. V., Fink, D., Johnson, S. W., Hamilton, T. C., Howell, S. B., Quantitation of platinum-DNA adduct repair in mismatch repair deficient and proficient human colorectal cancer cell lines using an in vitro DNA repair assay, Proc. Am. Assoc. Cancer Res. (1997), abstract, 38, 359. Jordan, P., Carmo-Fonseca, M., Molecular mechanisms involved in cisplatin cytotoxicity, Cell Mol. Life Sci. (2000), 57, 1229-1235. Kartalou, M., Essingmann, J. M., Mechanisms of resistance to cisplatin, Mutat. Res. (2001), 478, 23-43) or drug uptake/efflux (Kartalou, M., Essingmann, J. M., Mechanisms of resistance to cisplatin, Mutat. Res. (2001), 478, 23-43. Berger, W., Elbling, L., Hauptmann, E., Micksche, M., Expression of the multidrug resistance-associated protein (MRP) and chemoresistance of human non-small-cell lung cancer cells, Int. J. Cancer (1997), 73, 84-93. Borst, P., Kool, M., Evers, R., Do cMOAT (MRP2), other MRP homologues, and LRP play a role in MDR? Cancer Biol. (1997), 8, 205-213. Young, L. C., Campling, B. G., Voskoglou-Nomikos, T., Cole, S. P. C., Deeley, R. G., Gerlach, J. H., Expression of multidrug resistance protein-related genes in lung cancer: correlation with drug response, Clin. Cancer Res. (1999), 5, 673-480. Berger, W., Elbling, L., Micksche, M., Expression of the major vault protein LRP in human non-small-cell lung cancer cells: activation by short-term exposure to antineoplastic drugs, Int. J. Cancer (2000), 88, 293-300. Borst, P., Evers, R., Kool, M., Wijnholds, J., A family of drug transporters: the multidrug resistance-associated proteins, J Nat. Cancer Inst. (2000), 92, 1295-1302. Oguri, T., Isobe, T., Suzuki, T., Nishio, K., Fujiwara, Y., Katoh, O., Yamakido, M., Increased expression of the MRP5 gene is associated with exposure to platinum drugs in lung cancer, Int. J. Cancer (2000), 86, 95-100.

Current advances in technology, including microarrays and quantitative RT-PCR methods, are allowing classification of cancer types on the basis of functional genomics as opposed to histomorphology. Golub, T. R., Slonim, D. K., Tamayo, P., Huard, C., Gaasenbeek, M., Mesirov, J. P., Coller, H., Loh, M. L., Downing, J. R., Caligiuri, M. A., Bloomfield, C. D., Lander, E. S., Molecular classification of cancer: class discovery and class prediction by gene expression monitoring, Science (1999), 286, 531-537. Alizadeh, A. A., Eisen, M. B., Davis, R. E., Ma, C., Lossos, I. S., Rosenwald, A., Boldrick, J. C., Sabet, H., Tran, T., Yu, X., Powell, J. I., Yang, L., Marti, G. E., Moore, T., Hudson, Jr., J., Lu, L., Lewis, D. B., Tibshirani, R., Sherlock, G., Chan, W. C., Greiner, T. C., Weisenburger, D. D., Armitage, J. O., Warnke, R., Staudt, L. M., et al., Distinct types of diffuse large B-cell lymphoma identified by gene expression profiling, Nature (2000), 403, 503-511. For example, they may allow for the discovery of predictive markers based on gene expression profiles. Microarray screening analysis currently is being investigated to predict chemotherapeutic sensitivity based on gene expression profiles. Scherf, U., Ross, D. T., Waltham, M., Smith, L. H., Lee, J. K., Tanabe, L., Kohn, K. W., Reinhold, W. C., Myers, T. G., Andrews, D. T., Scudiero, D. A., Eisen, M. B., Sausville, E. A., Pommier, Y., Botstein, D., Brown, P. O., Weinstein, J. N., A gene expression database for the molecular pharmacology of cancer, Nat. Genet. (2000), 24, 236-244. Kihara, C. Tsunoda, T., Tanaka, T., Yamana, H., Furukawa, Y., Ono, K., Kitahara, O., Zembutsu, H., Yanagawa, R., Hirata, K., Takagi, T., Nakamura, Y., Prediction of sensitivity of esophageal tumors to adjuvant chemotherapy by cDNA microarray analysis of gene-expression profiles, Cancer Res. (2001), 61, 6474-6479. Zembutsu, H., Ohnishi, Y., Tsunoda, T., Furukawa, Y., Katagiri, T., Ueyama, Y., Tamaoki, N., Nomura, T., Kitahara, O., Yanagawa, R., Hirata, K., Nakamura, Y., Genome-wide cDNA microarray screening to correlate gene expression profiles with sensitivity of 85 human cancer xenografts to anticancer drugs, Cancer Res. (2002), 62, 518-527. An advantage of microarray analysis is that thousands of genes may be simultaneously evaluated. However, it is generally recognized that, due to lack of standardization, relatively low sensitivity and relatively poor lower thresholds of detection, microarray assessments need to be confirmed with follow-up quantitative methods. StaRT-PCR is a method that allows for rapid, reproducible, standardized, quantitative measurements for many genes simultaneously. Willey, J. C., Crawford, E. L., Jackson, C. M., Weaver, D. A., Hoban, J. C., Khuder, S. A., DeMuth, J. P., Expression measurement of many genes simultaneously by quantitative RT-PCR using standardized mixtures of competitive templates, Am. J. Respir. Cell Mol. Biol. (1998), 19, 6-17. Weaver, et al. Comparison of expression patterns by microarray and standardized RT-PCR analyses in lung cancer cell lines with varied sensitivity to carboplatin. Proc. Am. Assoc. Cancer Res. 2001 (abstract) 42, 606.

StaRT-PCR can also be used to more accurately diagnose lung cancer in small biopsy tissues. Warner, et al. "High c-myc×E2F-1/p21 may augment cytologic diagnosis of NSCLC" Prod. Am. Assoc. Cancer Res. Vol. 43, abstract 3738, March 2002; Weaver, et al. Gene expression modeling of cisplatin chemoresistance in non-small cell lung cancer cell lines utilizing standardized RT StarRT-PCR" Prod. Am. Assoc. Cancer Res. Vol. 43, abstract 5471, March 2002.

SUMMARY OF THE INVENTION

The present invention identifies patterns of individual, interactive gene expression and/or indices (IGEI) comprising the expression values of multiple genes which, in one instance, are more effective markers of chemoresistant non-small cell lung cancer (NSCLC) tumors than expression values of individual genes, and in another instance, may be used to more accurately diagnose lung cancer in small biopsy tissues.

The present invention is directed to the identification and use of markers that can be used to determine the sensitivity of cancer cells to a therapeutic agent. More specifically, the invention features "a number of markers" that are variably expressed in cancer tissue and can be used to determine the sensitivity of cancer cells to a therapeutic agent. Still more specifically, the invention features "interactive gene expression indices" (IGEI) useful for assessment of biological samples to prospectively identify the usefulness of therapeutic agents.

The present invention thus provides gene expression profiles which serve as useful diagnostic markers as well as markers that can be used to monitor disease states, disease progression, drug toxicity, drug efficacy and drug metabolism.

The present invention further provides a method to determine whether an agent or combination of agents can be used to reduce the growth of cancer cells as well as determining new agents for the treatment of cancer Various embodiments of the present invention are directed to uses of the identified markers whose expression is correlated with accurate diagnosis of lung cancer cells or tissue compared to normal tissues, and other markers whose expression is correlated with sensitivity to treatment with a therapeutic agent. In particular, the present invention provides, without limitation: 1) methods for determining whether a particular tissue is lung cancer or non cancer tissue; 2) methods for monitoring the effectiveness of therapeutic agents used for the treatment of cancer; 3) methods for developing new therapeutic agents for the treatment of cancer; and 4) methods for identifying combinations of therapeutic agents for the treatment of cancer.

By examining and quantifying the expression of one or more of the identified markers in a sample of cancer cells, it is further possible to determine which therapeutic agent or combination of agents will be most likely to reduce the growth rate of the cancer and can further be used in selecting appropriate treatment agents.

By examining and quantifying the expression of one or more of the identified markers in a sample of cancer cells, it is also possible to determine which therapeutic agent or combination of agents will be the least likely to reduce the growth rate of the cancer.

By examining and quantifying the expression of one or more of the identified markers, it is also possible to eliminate inappropriate therapeutic agents.

By examining and quantifying the expression of one or more identified markers when cancer cells or a cancer cell line is exposed to a potential anti-cancer agent, it is possible to identify the efficacy of new anti-cancer agents.

Further, by examining and quantifying the expression of one or more of the identified markers in a sample of cancer cells taken from a patient during the course of therapeutic treatment, it is possible to determine whether the therapeutic treatment is continuing to be effective or whether the cancer has become resistant (refractory) to the therapeutic treatment. These determinations can be made on a patient-by-patient basis or on an agent by agent (or combination of agents) basis. It may also be possible to determine whether or not a particular therapeutic treatment is likely to benefit a particular patient or group/class of patients, or whether a particular treatment should be continued.

The present invention further provides previously unknown or unrecognized targets for the development of anti-cancer agents, such as chemotherapeutic compounds.

The identified interactive gene expression indices (IGEI) of the present invention are useful as targets in developing treatments (either for a single agent or for multiple agents) for cancer.

The present invention identifies the global changes in gene expression associated with lung cancer by examining gene expression in tissue from normal lung. The present invention also identifies expression profiles which serve as useful diagnostic markers as well as markers that can be used to monitor disease states, disease progression, drug toxicity, drug efficacy and drug metabolism.

In some preferred embodiments, the methods, genes, and IGEI described herein are useful to identify cisplatin resistant cancers (in contrast to diagnosing cancers from normal tissues). Such embodiments may include detecting the expression level of one or more genes selected from a group consisting of ERCC2, ABCC5, XPA and XRCC1.

In some preferred embodiments, the method may include detecting the expression level of one or more genes selected from a group consisting of ERCC2/XPC, ABCC5/GTF2H2, ERCC2/GTF2H2, XPA/XPC and XRCC1/XPC.

In some preferred embodiments, the method may include detecting the expression level of one or more genes selected from a group consisting of ABCC5/GTF2H2, and ERCC2/GTF2H2.

The invention also includes methods of detecting the progression of NSCLC and/or differentiating small cell lung cancer (SCLC) and/or nonmetastatic from metastatic disease. For instance, methods of the invention include detecting the progression of NSCLC in a patient comprising the step of detecting the level of expression in a tissue sample of two or more genes from Tables 1 and/or 5; wherein differential expression of the genes in Tables 1 and/or 5 is indicative of NSCLC progression. In some preferred embodiments, one or more genes may be selected from a group consisting of the genes listed in Table 5.

In some aspects, the present invention provides a method of monitoring the treatment of a patient with NSCLC, comprising administering a pharmaceutical composition to the patient and preparing a gene expression profile from a cell or tissue sample from the patient and comparing the patient gene expression profile to a gene expression from a cell population comprising normal lung cells or to a gene expression profile from a cell population comprising lung cancer cells or to both. In some preferred embodiments, the gene profile will include the expression level of one or more genes in Tables 1 and 5. In other preferred embodiments, one or more genes may be selected from a group consisting of the genes listed in Table 5.

In another aspect, the present invention provides a method of treating a patient with NSCLC, comprising administering to the patient a pharmaceutical composition, wherein the composition alters the expression of at least one gene in Tables 1 and 5, preparing a gene expression profile from a cell or tissue sample from the patient comprising tumor cells and comparing the patient expression profile to a gene expression profile from an untreated cell population comprising NSCLC cells. In some preferred embodiments, one or more genes may be selected from a group consisting of the genes listed in Table 5.

The invention includes methods of diagnosing the presence or absence of lung cancer in a patient comprising the step of detecting the level of expression in a tissue sample of an IGEI comprising c-myc×E2F-1/p21 (Sequence ID Nos. 40-48 since each gene has 3 primer sequences) in which the c-myc gene expression value (molecules/$10^6$ β-actin molecules) is multiplied times the E2F-1 expression value and this product is divided by the p21 gene expression value.

The c-myc×E2F-1/p21 index may also be used as a marker for the monitoring of disease progression, for instance, the development of lung cancer. For instance, a lung tissue sample or other sample from a patient may be assayed by any of the methods described herein, and the expression levels in the sample of c-myc×E2F-1/p21 may be compared to the expression levels found in normal lung tissue, tissue from SCLC, metastatic lung cancer or NSCLC tissue. Comparison of the expression data, as well as available sequence or other information may be done by researcher or diagnostician or may be done with the aid of a computer and databases as described herein.

The invention further includes methods of screening for an agent capable of modulating the onset or progression of NSCLC, comprising the steps of exposing a cell to the agent; and detecting the expression level of the c-myc×E2F-1/p21 index.

According to one aspect of the present invention, the genes identified in Tables 1 and 5 may be used as markers to evaluate the effects of a candidate drug or agent on a cell or tissue sample, for instance, a lung cancer cell or tissue sample. A candidate drug or agent can be screened for the ability to simulate the transcription or expression of a given marker or set of marker genes (drug targets) or to down-regulate or counteract the transcription or expression of a marker or markers. According to the present invention, one can also compare the specificity of drugs' effects on gene expression markers and comparing them. More specific drugs may have fewer transcriptional targets. Similar sets of markers identified for two drugs indicate a similarity of effects.

Any of the methods of the invention described above may include the detection and quantification of at least 2 genes from the Tables 1 and/or 5 or c-myc×E2F-1/p21. Preferred methods may detect and quantify all or nearly all of the genes in the tables. In some preferred embodiments, one or more genes may be selected from a group consisting of the genes listed in Table 5.

According to another aspect, the present invention relates to a method of diagnosing non small cell lung cancer in a patient, comprising: (a) detecting and quantifying the level of expression in a tissue sample of c-myc, E2F-1 and p21 genes; wherein differential expression of the c-myc, E2F-1 and p21 genes is indicative of non small cell lung cancer.

In another aspect, the present invention relates to a method of detecting the progression of non small cell lung cancer in a patient, comprising: (a) detecting and quantifying the level of expression in a tissue sample of c-myc, E2F-1 and p21 genes; wherein differential expression of the c-myc, E2F-1 and p21 genes is indicative of non small cell lung cancer progression.

In still other aspects, the present invention relates to a method of monitoring the treatment of a patient with non small cell lung cancer, comprising: (a) administering a pharmaceutical composition to the patient; (b) preparing a gene expression profile from a cell or tissue sample from the patient; and (c) comparing the patient gene expression profile to a gene expression from a cell population selected from the group consisting of normal lung cells, and non small cell lung cancer.

In still more aspects, the present invention relates to a method of treating a patient with non small cell lung cancer, comprising: (a) administering to the patient a pharmaceutical composition, wherein the composition alters the expression of at least one gene in Tables 1 and 5 or c-myc, E2F-1 and p21 genes; (b) preparing an IGEI comprising standardized gene expression values using StaRT-PCR from a cell or tissue sample comprising tumor cells obtained before treatment and another sample obtained after treatment; and (c) comparing the sample obtained prior to treatment with the sample obtained after treatment.

Yet other aspects of the present invention relate to a method of screening for an agent capable of modulating the onset or progression of non small cell lung cancer, comprising: (a) preparing a first IGEI comprising standardized gene expression values using StaRT-PCR of a cell population comprising non small cell cancer cells, wherein the first IGEI determines the expression level of one or more genes from Tables 1 and 5 or c-myc, E2F-2 and p21 genes; (b) exposing the cell population to the agent; (c) preparing second IGEI comprising standardized gene expression values using StaRT-PCR of the agent-exposed cell population; and (d) comparing the first and second IGEIs.

In another aspect, the present invention relates to one or more solid phase hybridization templates for measuring, in a standardized fashion, PCR products following standardized quantitative RT-PCR where the template is formed as follows:
   a) preparing at least one solid phase hybridization template where, for each gene, an oligonucleotide of any length that will bind with specificity to both the competitive template, CT, and native template, NT, is spotted to a filter;
   b) identifying a suitable oligonucleotide such that the region between the forward primer (common to both the NT and CT) and the 3' 20 bp of the reverse CT primer is evaluated;
   c) attaching an oligonucleotide to a solid support at a previously designated location;
   d) amplifying the CT and NT PCR products and hybridizing to the spots of the filter wherein each gene (NT and CT) are amplified separately;
   e) pooling the PCR products for hybridization; and
   f) preparing two oligonucleotide probes, each labeled with a different fluor, for each gene wherein one oligonucleotide is homologous to, and will bind to sequences unique to the NT for a gene that was PCR-amplified such that this oligonucleotide binds to the region of the NT that is not homologous to the CT and is labeled with a different fluor, and wherein the other oligonucleotide is specific to the CT and is labeled with a different fluor such that this other oligonucleotide is homologous to and will bind to CT sequences that span the 3' end of the reverse primer. In certain embodiments, the NT-specific and CT-specific oligonucleotides for multiple genes are mixed in equal amounts and hybridized to the gene-specific PCR products bound to the gene-specific oligonucleotides spotted on the filter. Also, the ratio between the fluors bound to the spot quantify the NT relative to CT. Although there may be different binding affinities between the CT and CT probe relative to that between the NT and NT probe, this difference is consistent between different samples assessed, and from one experiment to another. It should be noted that the template can comprises at least one standardized microarray, microbeads, glass slides, or chips prepared by photolithography, and that the solid support can be a membrane, a glass support, a filter, a tissue culture dish, a polymeric material, a bead and a silica support. In certain embodiments, the solid support comprising at least two oligonucleotides, wherein each of the oligonucleotides comprises a sequence that specifically hybridizes to at least one gene in Tables 1 and 5 or the c-myc, E2F-1 and p21 genes. It should also be noted that the oligonucleotides can be covalently attached to the solid support, or alternatively can be non-covalently attached to the solid support expression level in units of molecules/$10^6$ β-actin molecules for the set of genes in normal lung tissue.

The invention further includes computer systems comprising a numerical standardized database containing information identifying the expression level in lung tissue of a set of genes comprising at least two genes in Tables 1 and 5 or c-myc×E2F-1/p21; and a user interface to view the information. In some preferred embodiments, one or more genes may be selected from a group consisting of the genes listed in Table 5. The numerical standardized database may further include sequence information for the genes, information identifying the expression level for the set of genes in normal lung tissue and malignant tissue (metastatic and nonmetastatic) and may contain links to external databases such as GenBank.

The invention further comprises kits useful for the practice of one or more of the methods of the invention. In some preferred embodiments, a kit may contain one or more solid supports having attached thereto one or more oligonucleotides. The solid support may be a high-density oligonucleotide array. Kits may further comprise one or more reagents for use with the arrays, one or more signal detection and/or array-processing instruments, one or more gene expression databases and one or more analysis and database management software packages. The kits, in certain preferred embodiments, have StaRT-PCR reagents with reagents to apply to standardized microarrays.

The invention still further includes methods of using the databases, such as methods of using the disclosed computer systems to present information identifying the expression level in a tissue or cell of at least one gene in Tables 1 and 5, comprising the step of comparing the expression level of at least one gene in Tables 1 and 5 in the tissue or cell to the level of expression of the gene in the database. In some preferred embodiments, one or more genes may be selected from a group consisting of the genes listed in Table 5.

Other features and advantages of the invention will be apparent from the detailed description and from the claims. Although materials and methods similar or equivalent to those described herein can be used in the practice or testing of the invention, the preferred materials and methods are described below.

BRIEF DESCRIPTION OF THE DRAWINGS

FIGS. 1a and 1b are a Table 1 showing primers used for PCR amplification. Table 1 shows primers used for PCR amplification including the gene designation, GenBank accession number, Sequence ID number, primer, sequence, bp position in cDNA, and product length (bp).

The sequences of the expression marker genes are in the public databases. Tables 1 and 5 provide the GenBank accession number for the genes. The sequences of the genes in GenBank are expressly incorporated by reference as are equivalent and related sequences present in GenBank or other public databases. The column labeled "SEQ ID" refers to the sequence identification number correlating the listed gene to its sequence information as provided within the sequence listing of this application.

FIG. 2 is a Table 2 showing the IC 50 for NSCLC cell lines and the cisplatin levels.

FIGS. 3a and 3b are a Table 3 showing the gene expression in NSCLC cell lines (mRNAs/$10^6$ ACTB mRNAs).

FIG. 4 is a Table 4 showing the correlation of gene expression with cisplatin chemoresistance in NSCLC cell lines.

FIG. 5 is a Table 5 showing the statistical assessments of cisplatin chemoresistance models in NSCLC cell lines.

FIG. 6 is a Table 6 the effect of collection methods on RNA quality in H1155 human NSCLC cells in Example II which relates to IEGI used for Fine Needle Analysis (FNA) for lung cancer diagnosis.

FIG. 7 is a Table 7 showing cytological information and diagnosis of FNA specimen cells in Example.

FIG. 8 is a Table 8 showing gene expression value and index values for c-myc, E2F-1 and p21 in FNA samples.

FIGS. 9a and 9b are schematic illustrations of an analysis of standardized RT-PCR products with microarrays and microbeads: FIG. 9a shows microarrays where the identity of the gene is known by the location of the microarray; and FIG. 9b shows microbeads where the identity of the gene is known by the fluorescent color of the bead.

DETAILED DESCRIPTION OF THE PREFERRED EMBODIMENTS

The present invention is based, in part, on the identification and quantification of markers that can be used to determine whether cancer cells are sensitive to a therapeutic agent. Based on these identifications and quantifications, the present invention provides, without limitation: 1) methods for determining whether a therapeutic agent (or combination of agents) will or will not be effective in stopping or slowing tumor growth; 2) methods for monitoring the effectiveness of a therapeutic agent (or combination of agents) used for the treatment of cancer; 3) methods for identifying new therapeutic agents for the treatment of cancer; 4) methods for identifying combinations of therapeutic agents for use in treating cancer; 5) methods for identifying specific therapeutic agents and combinations of therapeutic agents that are effective for the treatment of cancer in specific patients; and methods for diagnosing cancer.

Definitions

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, the preferred methods and materials are described herein. All publications, patent applications, patents, and other references mentioned herein are incorporated by reference in their entirety. The content of all GenBank, and other database records such as IMAGE Consortium, and Unigene database records cited throughout this application (including the Tables) are also hereby incorporated by reference. In the case of conflict, the present specification, including definitions, will control. In addition, the materials, methods, and examples are illustrative only and are not intended to be limiting.

The articles "a" and "an" are used herein to refer to one or to more than one (i.e. to at least one) of the grammatical object of the article. By way of example, "an element" means one element or more than one element.

A "marker" is a naturally occurring polymer corresponding to at least one of the nucleic acids listed in Tables 1-5. For example, markers include, without limitation, sense and antisense strands of genomic DNA (i.e. including any introns occurring therein), RNA generated by transcription of genomic DNA (i.e. prior to splicing), RNA generated by splicing of RNA transcribed from genomic DNA, and proteins generated by translation of spliced RNA (i.e. including proteins both before and after cleavage of normally cleaved regions such as transmembrane signal sequences). As used herein, "marker" may also include a cDNA made by reverse transcription of an RNA generated by transcription of genomic DNA (including spliced RNA).

The term "probe" refers to any molecule which is capable of selectively binding to a specifically intended target molecule, for example a marker of the invention. Probes can be either synthesized by one skilled in the art, or derived from appropriate biological preparations. For purposes of detection of the target molecule, probes may be specifically designed to be labeled, as described herein. Examples of molecules that can be utilized as probes include, but are not limited to, RNA, DNA, proteins, antibodies, and organic monomers.

The "normal" level of expression of a marker is the level of expression of the marker in cells of a patient not afflicted with cancer.

As used herein, the term "promoter/regulatory sequence" means a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue-specific manner.

A "constitutive" promoter is a nucleotide sequence which, when operably linked with a polynucleotide which encodes or specifies a gene product, causes the gene product to be produced in a living human cell under most or all physiological conditions of the cell.

A "transcribed polynucleotide" is a polynucleotide (e.g. an RNA, a cDNA, or an analog of one of an RNA or cDNA) which is complementary to or homologous with all or a portion of a mature RNA made by transcription of a genomic DNA corresponding to a marker of the invention and normal post-transcriptional processing (e.g. splicing), if any, of the transcript.

"Complementary" refers to the broad concept of sequence complementarity between regions of two nucleic acid strands or between two regions of the same nucleic acid strand. It is known that an adenine residue of a first nucleic acid region is capable of forming specific hydrogen bonds ("base pairing") with a residue of a second nucleic acid region which is antiparallel to the first region if the residue is thymine or uracil. Similarly, it is known that a cytosine residue of a first nucleic acid strand is capable of base pairing with a residue of a second nucleic acid strand which is antiparallel to the first strand if the residue is guanine. A first region of a nucleic acid is complementary to a second region of the same or a different nucleic acid if, when the two regions are arranged in an antiparallel fashion, at least one nucleotide residue of the first region is capable of base pairing with a residue of the second region. Preferably, the first region comprises a first portion and the second region comprises a second portion, whereby, when the first and second portions are arranged in an antiparallel fashion, at least about 50%, and preferably at least about 75%, at least about 90%, or at least about 95% of the nucleotide residues of the first portion are capable of base pairing with nucleotide residues in the second portion. More preferably, all nucleotide residues of the first portion are capable of base pairing with nucleotide residues in the second portion.

"Homologous" as used herein, refers to nucleotide sequence similarity between two regions of the same nucleic acid strand or between regions of two different nucleic acid strands. When a nucleotide residue position in both regions is occupied by the same nucleotide residue, then the regions are homologous at that position. A first region is homologous to a second region if at least one nucleotide residue position of each region is occupied by the same residue. Homology between two regions is expressed in terms of the proportion of nucleotide residue positions of the two regions that are occupied by the same nucleotide residue. Preferably, the first region comprises a first portion and the second region comprises a second portion, whereby, at least about 50%, and preferably at least about 75%, at least about 90%, or at least about 95% of the nucleotide residue positions of each of the portions are occupied by the same nucleotide residue. More preferably, all nucleotide residue positions of each of the portions are occupied by the same nucleotide residue.

A marker is "fixed" to a substrate if it is covalently or non-covalently associated with the substrate such the substrate can be rinsed with a fluid (e.g. standard saline citrate, pH 7.4) without a substantial fraction of the marker dissociating from the substrate.

As used herein, a "naturally-occurring" nucleic acid molecule refers to an RNA or DNA molecule having a nucleotide sequence that occurs in nature (e.g. encodes a natural protein).

Cancer is "inhibited" if at least one symptom of the cancer is alleviated, terminated, slowed, or prevented. As used herein, cancer is also "inhibited" if recurrence or metastasis of the cancer is reduced, slowed, delayed, or prevented. Cancer is also inhibited or the cell proliferation decreases or the cell death rate increases A "kit" is any manufacture (e.g. a package or container) comprising at least one reagent, e.g. a probe, for specifically detecting a marker of the invention, the manufacture being promoted, distributed, or sold as a unit for performing the methods of the present invention.

Specific Embodiments

The examples provided below concern the identification and quantification of markers that distinguish in cancer cell lines that are sensitive to defined chemotherapeutic agents, namely platinum compounds from those that are not responsive. Accordingly, one or more of the markers can be used to identify cancer cells that can be successfully treated by that agent. A change in the expression in one or more of the markers can also be used to identify cancer cells that cannot be successfully treated by that agent. These markers can therefore be used in methods for identifying cancers that have become or are at risk of becoming refractory to treatment with the agent.

The expression level of the identified markers may be used to: 1) determine if a cancer can be treated by an agent or combination of agents; 2) determine if a cancer is responding to treatment with an agent or combination of agents; 3) select an appropriate agent or combination of agents for treating a cancer; 4) monitor the effectiveness of an ongoing treatment; and 5) identify new cancer treatments (either single agent or combination of agents).

In particular, the identified markers may be utilized to determine appropriate therapy, to monitor clinical therapy and human trials of a drug being tested for efficacy, and to develop new agents and therapeutic combinations.

Accordingly, the present invention provides methods for determining whether an agent can be used to inhibit cancer cells, comprising the steps of:
 a) obtaining a sample of cancer cells;
 b) determining and quantifying the level of expression in the cancer cells of a marker identified in Tables 1 and 5; and
 c) identifying that an agent can be used to inhibit the cancer cells when the marker is expressed at a certain level.

The present invention also provides methods for determining whether an agent is effective in treating cancer, comprising the steps of:
 a) obtaining a sample of cancer cells;
 b) exposing the sample to an agent;
 c) determining and quantifying the level of expression of a marker identified in Tables 1 and 5 in the sample exposed to the agent and in a sample that is not exposed to the agent; and
 d) identifying that an agent is effective in treating cancer when expression of the marker is altered in the presence of the agent.

The present invention further provides methods for determining whether treatment with an agent should be continued in a cancer patient, comprising the steps of:
 a) obtaining two or more samples comprising cancer cells from a patient during the course of treatment with the agent;
 b) determining and quantifying the level of expression of a marker identified in Tables 1 and 5 in the two or more samples; and
 c) continuing treatment when the expression level of the marker is at a certain level, e.g., not significantly altered during the course of treatment.

The present invention also provides methods of identifying new cancer treatments, comprising the steps of:
 a) obtaining a sample of cancer cells;
 b) determining and quantifying the level of expression of a marker identified in Tables 1 and 5;
 c) exposing the sample to the cancer treatment;
 d) determining the level of expression of the marker in the sample exposed to the cancer treatment; and
 e) identifying that the cancer treatment is effective in treating cancer when the marker is expressed at a certain level.

Accordingly, in another aspect, the present invention provides methods for diagnosing cancer, comprising the steps of:
 a) obtaining a sample of tissue that might contain cancer cells; and
 b) determining and quantifying the level of expression in the tissue the c-mcy×E2F-1/p21 index.

As used herein, an agent is said to reduce the rate of growth of cancer cells when the agent can reduce at least 50%, preferably at least 75%, most preferably at least 95% of the growth of the cancer cells. Such inhibition can further include a reduction in survivability and an increase in the rate of death of the cancer cells. The amount of agent used for this determination will vary based on the agent selected. Typically, the amount will be a predefined therapeutic amount.

As used herein, the term "agent" is defined broadly as anything that cancer cells may be exposed to in a therapeutic protocol. In the context of the present invention, such agents include, but are not limited to, chemotherapeutic agents, such as anti-metabolic agents, e.g., cross-linking agents, e.g., cis-platin and CBDCA, radiation and ultraviolet light.

Further to the above, the language "chemotherapeutic agent" is intended to include chemical reagents which inhibit the growth of proliferating cells or tissues wherein the growth of such cells or tissues is undesirable.

The agents tested in the present methods can be a single agent or a combination of agents. For example, the present methods can be used to determine whether a single chemotherapeutic agent, such as cisplatin, can be used to treat a cancer or whether a combination of two or more agents can be used. Preferred combinations will include agents that have different mechanisms of action, e.g., the use of an anti-mitotic agent in combination with an alkylating agent.

As used herein, cancer cells refer to cells that divide at an abnormal (increased) rate. In particular, the cancer cells include, but are not limited to, non-small cell lung cancer (NSCLC). The source of the cancer cells used in the present method will be based on how the method of the present invention is being used. For example, if the method is being used to determine whether a patient's cancer can be treated with an agent, or a combination of agents, then the preferred source of cancer cells will be cancer cells obtained from a cancer biopsy from the patient. Alternatively, a cancer cell line similar to the type of cancer being treated can be assayed. For example if non-small cell lung cancer (NSCLC) is being treated, then a (NSCLC) cell line can be used. If the method is being used to monitor the effectiveness of a therapeutic protocol, then a tissue sample from the patient being treated is the preferred source. If the method is being used to identify new therapeutic agents or combinations, any cancer cells, e.g., cells of a cancer cell line, can be used.

A skilled artisan can readily select and obtain the appropriate cancer cells that are used in the present method. For cancer cell lines, sources such as The National Cancer Institute, for the NCI cells used in the examples, are preferred. For cancer cells obtained from a patient, standard biopsy methods, such as a needle biopsy, can be employed, taking necessary precautions known in the art to preserve mRNA integrity.

In the methods of the present invention, the level or amount of expression of one or more markers selected from the group consisting of the markers identified in Table 1 is determined. As used herein, the level or amount of expression refers to the level of expression of an mRNA encoded by the gene or the level of expression of the protein encoded by the gene (i.e., whether or not expression is or is not occurring in the cancer cells). It also may refer to the values of the interactive gene expression indices (IGEI) disclosed herein. A skilled artisan can readily adapt known mRNA detection methods for use in detecting the level of mRNA encoded by one or more of the (IGEI) marker sets of the present invention.

Proteins from cancer cells can be isolated using techniques that are well known to those of skill in the art. The protein isolation methods employed can, for example, be such as those described in Harlow and Lane (Harlow and Lane, 1988, Antibodies: A Laboratory Manual, Cold Spring Harbor Laboratory Press, Cold Spring Harbor, N.Y.).

A variety of formats can be employed to determine whether a sample contains a protein that binds to a given antibody. Examples of such formats include, but are not limited to, enzyme immunoassay (EIA), radioimmunoassay (RIA), Western blot analysis and enzyme linked immunoabsorbant assay (ELISA). A skilled artisan can readily adapt known protein/antibody detection methods for use in determining whether cancer cells expresses a protein encoded by one or more of the (IGEI) marker sets of the present invention.

In one format, antibodies, or antibody fragments, can be used in methods such as Western blots or immunofluorescence techniques to detect the expressed proteins. In such uses, it is generally preferable to immobilize either the antibody or protein on a solid support. Suitable solid phase supports or carriers include any support capable of binding an antigen or an antibody. Well-known supports or carriers include glass, polystyrene, polypropylene, polyethylene, dextran, nylon, amylases, natural and modified celluloses, polyacrylamides, gabbros, and magnetite. In addition, the solid support can be selected from a membrane, a glass support, a filter, a tissue culture dish, a polymeric material, a bead and a silica support.

In certain embodiments, the solid support comprising at least two oligonucleotides, wherein each of the oligonucleotides comprises a sequence that specifically hybridizes to at least one gene in Tables 1 and 5. Also, the solid support can include oligonucleotides that are covalently attached to the solid support, or alternatively, are non-covalently attached to the solid support.

One skilled in the art will know many other suitable carriers for binding antibody or antigen, and will be able to adapt such support for use with the present invention. For example, protein isolated from cancer cells can be run on a polyacrylamide gel electrophoresis and immobilized onto a solid phase support such as nitrocellulose. The support can then be washed with suitable buffers followed by treatment with the detectably labeled marker product specific antibody. The solid phase support can then be washed with the buffer a second time to remove unbound antibody. The amount of bound label on the solid support can then be detected by conventional means.

Another embodiment of the present invention includes a step of detecting whether an agent stimulates the expression of one or more of the (IGEI) marker sets of the present invention. Although some of the present (IGEI) marker sets can be expressed in non-treated cancer cells, treatment with an agent may, or may not, alter expression. Alterations in the expression level of the (IGEI) marker sets of the present invention can provide a further indication as to whether an agent will or will not be effective at reducing the growth rate of the cancer cells.

In such a use, the present invention provides methods for determining whether an agent, e.g., a chemotherapeutic agent, can be used to inhibit cancer cells comprising the steps of:
 a) obtaining a sample of cancer cells;
 b) exposing the sample of cancer cells to one or more test agents;
 c) determining and quantifying the level of expression in the cancer cells of one or more markers selected from the group consisting of the markers identified in Table1 in the sample exposed to the agent and in a sample of cancer cells that is not exposed to the agent; and
 d) identifying that an agent can be used to treat the cancer when the expression of one or more of the markers is increased in the presence of said agent and/or when the expression of one or more of the markers is not increased in the presence of said agent.

This embodiment of the methods of the present invention involves the step of exposing the cancer cells to an agent. The method used for exposing the cancer cells to the agent will be based primarily on the source and nature of the cancer cells and the agent being tested. The contacting can be performed in vitro or in vivo, in a patient being treated/evaluated or in animal model of a cancer. For cancer cells and cell lines and chemical compounds, exposing the cancer cells involves contacting the cancer cells with the compound, such as in tissue culture media. A skilled artisan can readily adapt an appropriate procedure for contacting cancer cells with any particular agent or combination of agents.

As discussed above, the identified (IGEI) marker sets can also be used to assess whether a tumor has become refractory to an ongoing treatment (e.g., a chemotherapeutic treatment). When a tumor is no longer responding to a treatment the expression profile of the tumor cells will change: the level of expression of one or more of the markers will be reduced and/or the level of expression of one or more of the markers will increase.

In such a use, the invention provides methods for determining whether an anti-cancer treatment should be continued in a cancer patient, comprising the steps of:
 a) obtaining two or more samples of cancer cells from a patient undergoing anti-cancer therapy;
 b) determining and quantifying the level of expression of one or more markers selected from the group and one or more of the corresponding (IGEI) marker sets in the sample exposed to the agent and in a sample of cancer cells that is not exposed to the agent; and
 c) discontinuing treatment when the expression of one or more (IGEI) marker sets is altered.

As used herein, a patient refers to any subject undergoing treatment for cancer. The preferred subject will be a human patient undergoing chemotherapy treatment.

This embodiment of the present invention relies on comparing two or more samples obtained from a patient undergoing anti-cancer treatment. In general, it is preferable to obtain a first sample from the patient prior to beginning therapy and one or more samples during treatment. In such a use, a baseline of expression prior to therapy is determined and then changes in the baseline state of expression are monitored during the course of therapy. Alternatively, two or more successive samples obtained during treatment can be used without the need of a pre-treatment baseline sample. In such a use, the first sample obtained from the subject is used as a baseline for determining whether the expression of a particular marker is increasing or decreasing.

In general, when monitoring the effectiveness of a therapeutic treatment, two or more samples from the patient are examined. Preferably, three or more successively obtained samples are used, including at least one pretreatment sample.

The present invention further provides kits comprising compartmentalized containers comprising reagents for detecting one or more, preferably two or more, of the markers and/or (IGEI) marker sets of the present invention. As used herein a kit is defined as a pre-packaged set of containers into which reagents are placed. The reagents included in the kit comprise probes/primers and/or antibodies for use in detecting (IGEI) marker sets expression. In addition, the kits of the present invention may preferably contain instructions which describe a suitable detection assay. Such kits can be conveniently used, e.g., in clinical settings, to diagnose patients exhibiting symptoms of cancer.

Various aspects of the invention are described in further detail in the following subsections.

Nucleic Acid Samples

It is apparent to one of ordinary skill in the art, nucleic acid samples used in the methods and assays of the invention may be prepared by any available method or process. Methods of isolating total mRNA are also well known to those of skill in the art. Such samples include RNA samples, but also include cDNA synthesized from an mRNA sample isolated from a cell or tissue of interest. Such samples also include DNA amplified from the cDNA, and an RNA transcribed from the amplified DNA. One of skill in the art would appreciate that it is desirable to inhibit or destroy RNase present in homogenates before homogenates can be used.

Biological samples may be of any biological tissue or fluid or cells from any organism as well as cells raised in vitro, such as cell lines and tissue culture cells. Frequently the sample will be a "clinical sample" which is a sample derived from a patient. Typical clinical samples include, but are not limited to, sputum, blood, blood-cells (e.g., white cells), tissue or fine needle biopsy samples, urine, peritoneal fluid, and pleural fluid, or cells therefrom. Biological samples may also include sections of tissues, such as frozen sections or formalin fixed sections taken for histological purposes.

Thus, one aspect of the invention pertains to isolated nucleic acid molecules that correspond to a marker of the invention, including nucleic acids which encode a polypeptide corresponding to a marker of the invention or a portion of such a polypeptide. Isolated nucleic acids of the invention also include nucleic acid molecules sufficient for use as hybridization probes to identify nucleic acid molecules that correspond to a marker of the invention, including nucleic acids which encode a polypeptide corresponding to a marker of the invention, and fragments of such nucleic acid molecules, e.g., those suitable for use as PCR primers for the amplification or mutation of nucleic acid molecules. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

An "isolated" nucleic acid molecule is one which is separated from other nucleic acid molecules which are present in the natural source of the nucleic acid molecule. Preferably, an "isolated" nucleic acid molecule is free of sequences (preferably protein-encoding sequences) which naturally flank the nucleic acid (i.e., sequences located at the 5' and 3' ends of the nucleic acid) in the genomic DNA of the organism from which the nucleic acid is derived.

A nucleic acid molecule of the present invention, e.g., a nucleic acid encoding a protein corresponding to a marker listed in Table 1, can be isolated using standard molecular biology techniques and the sequence information in the database records described herein. Using all or a portion of such nucleic acid sequences, nucleic acid molecules of the invention can be isolated using standard hybridization and cloning techniques (e.g., as described in Sambrook et al., ed., Molecular Cloning: A Laboratory Manual, 2nd ed., Cold Spring Harbor Laboratory Press, Cold Spring Harbor, N.Y., 1989).

A nucleic acid molecule of the invention can be amplified using cDNA, mRNA, or genomic DNA as a template and appropriate oligonucleotide primers according to standard PCR amplification techniques. The nucleic acid so amplified can be cloned into an appropriate vector and characterized by DNA sequence analysis. Furthermore, oligonucleotides corresponding to all or a portion of a nucleic acid molecule of the invention can be prepared by standard synthetic techniques, e.g., using an automated DNA synthesizer.

In another preferred embodiment, an isolated nucleic acid molecule of the invention comprises a nucleic acid molecule which has a nucleotide sequence complementary to the nucleotide sequence of a nucleic acid corresponding to a marker of the invention or to the nucleotide sequence of a nucleic acid encoding a protein which corresponds to a marker of the invention. A nucleic acid molecule which is complementary to a given nucleotide sequence is one which is sufficiently complementary to the given nucleotide sequence that it can hybridize to the given nucleotide sequence thereby forming a stable duplex.

Moreover, a nucleic acid molecule of the invention can comprise only a portion of a nucleic acid sequence, wherein the full length nucleic acid sequence comprises a marker of the invention or which encodes a polypeptide corresponding to a marker of the invention. Such nucleic acids can be used, for example, as a probe or primer. The probe/primer typically is used as one or more substantially purified oligonucleotides. The oligonucleotide typically comprises a region of nucleotide sequence that hybridizes under stringent conditions to at least about 7, preferably about 12 or more consecutive nucleotides of a nucleic acid of the invention.

Probes based on the sequence of a nucleic acid molecule of the invention can be used to detect transcripts or genomic sequences corresponding to one or more markers of the invention. The probe comprises a label group attached thereto, e.g., a radioisotope, a fluorescent compound, an enzyme, or an enzyme co-factor. Such probes can be used as part of a diagnostic test kit for identifying cells or tissues which mis-express the protein, such as by measuring levels of a nucleic acid molecule encoding the protein in a sample of cells from a subject, e.g., detecting mRNA levels or determining whether a gene encoding the protein has been mutated or deleted.

The invention further encompasses nucleic acid molecules that differ, due to degeneracy of the genetic code, from the nucleotide sequence of nucleic acids encoding a protein which corresponds to a marker of the invention, and thus encode the same protein.

In addition to the nucleotide sequences described in the GenBank database records described herein, it will be appreciated by those skilled in the art that DNA sequence polymorphisms that lead to changes in the amino acid sequence can exist within a population (e.g., the human population). Such genetic polymorphisms can exist among individuals within a population due to natural allelic variation. An allele is one of a group of genes which occur alternatively at a given genetic locus. In addition, it will be appreciated that DNA polymorphisms that affect RNA expression levels can also exist that may affect the overall expression level of that gene (e.g., by affecting regulation or degradation).

As used herein, the phrase "allelic variant" refers to a nucleotide sequence which occurs at a given locus or to a polypeptide encoded by the nucleotide sequence.

As used herein, the terms "gene" and "recombinant gene" refer to nucleic acid molecules comprising an open reading frame encoding a polypeptide corresponding to a marker of the invention. Such natural allelic variations can typically result in 1-5% variance in the nucleotide sequence of a given gene. Alternative alleles can be identified by sequencing the gene of interest in a number of different individuals. This can be readily carried out by using hybridization probes to identify the same genetic locus in a variety of individuals. Any and all such nucleotide variations and resulting amino acid polymorphisms or variations that are the result of natural allelic variation and that do not alter the functional activity are intended to be within the scope of the invention.

In another embodiment, an isolated nucleic acid molecule of the invention is at least 7, 15, 20, 25, 30, 40, 60, 80, 100, 150, 200, 250, 300, 350, 400, 450, 550, 650, 700, 800, 900, 1000, 1200, 1400, 1600, 1800, 2000, 2200, 2400, 2600, 2800, 3000, 3500, 4000, 4500, or more nucleotides in length and hybridizes under stringent conditions to a nucleic acid corresponding to a marker of the invention or to a nucleic acid encoding a protein corresponding to a marker of the invention. As used herein, the term "hybridizes under stringent conditions" is intended to describe conditions for hybridization and washing under which nucleotide sequences at least 60% (65%, 70%, preferably 75%) identical to each other typically remain hybridized to each other. Such stringent conditions are known to those skilled in the art and can be found in sections 6.3.1-6.3.6 of Current Protocols in Molecular Biology, John Wiley & Sons, N.Y. (1989). A preferred, non-limiting example of stringent hybridization conditions are hybridization in 6.times. sodium chloride/sodium citrate (SSC) at about 45 degree C., followed by one or more washes in 0.2.times. SSC, 0.1% SDS at 50-65 degree C.

In addition to naturally-occurring allelic variants of a nucleic acid molecule of the invention that can exist in the population, the skilled artisan will further appreciate that sequence changes can be introduced by mutation thereby leading to changes in the amino acid sequence of the encoded protein, without altering the biological activity of the protein encoded thereby. For example, one can make nucleotide substitutions leading to amino acid substitutions at "non-essential" amino acid residues. A "non-essential" amino acid residue is a residue that can be altered from the wild-type sequence without altering the biological activity, whereas an "essential" amino acid residue is required for biological activity. For example, amino acid residues that are not conserved or only semi-conserved among homologs of various species may be non-essential for activity and thus would be likely targets for alteration. Alternatively, amino acid residues that are conserved among the homologs of various species (e.g., murine and human) may be essential for activity and thus would not be likely targets for alteration.

Accordingly, another aspect of the invention pertains to nucleic acid molecules encoding a polypeptide of the invention that contain changes in amino acid residues that are not essential for activity. Such polypeptides differ in amino acid sequence from the naturally-occurring proteins which correspond to the markers of the invention, yet retain biological activity. In one embodiment, such a protein has an amino acid sequence that is at least about 40% identical, 50%, 60%, 70%, 80%, 90%, 95%, or 98% identical to the amino acid sequence of one of the proteins which correspond to the markers of the invention.

An isolated nucleic acid molecule encoding a variant protein can be created by introducing one or more nucleotide substitutions, additions or deletions into the nucleotide sequence of nucleic acids of the invention, such that one or more amino acid residue substitutions, additions, or deletions are introduced into the encoded protein. Mutations can be introduced by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), non-polar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Alternatively, mutations can be introduced randomly along all or part of the coding sequence, such as by saturation mutagenesis, and the resultant mutants can be screened for biological activity to identify mutants that retain activity. Following mutagenesis, the encoded protein can be expressed recombinantly and the activity of the protein can be determined.

The present invention encompasses antisense nucleic acid molecules, i.e., molecules which are complementary to a sense nucleic acid of the invention, e.g., complementary to the coding strand of a double-stranded cDNA molecule corresponding to a marker of the invention or complementary to an mRNA sequence corresponding to a marker of the invention. Accordingly, an antisense nucleic acid of the invention can hydrogen bond to (i.e. anneal with) a sense nucleic acid of the invention. The antisense nucleic acid can be complementary to an entire coding strand, or to only a portion thereof, e.g., all or part of the protein coding region (or open reading frame). An antisense nucleic acid molecule can also be antisense to all or part of a non-coding region of the coding strand of a nucleotide sequence encoding a polypeptide of the invention. The non-coding regions ("5' and 3' untranslated regions") are the 5' and 3' sequences which flank the coding region and are not translated into amino acids.

An antisense oligonucleotide can be, for example, about 5, 10, 15, 20, 25, 30, 35, 40, 45, or 50 or more nucleotides in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl)uracil, 5-carboxymethylaminomethyl-2-thiouridin-e, 5 carboxymethylaminomethyl-uracil, dihydrouracil, beta-D-galactosylqueosine, inosine, N6-isopentenyl-adenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyamino-methyl-2-thiour-acil, beta-D-mannosylqueosine, 5'-methoxycarboxy-methyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA encoding a polypeptide corresponding to a selected marker of the invention to thereby inhibit expression of the marker, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. Examples of a route of administration of antisense nucleic acid molecules of the invention includes direct injection at a tissue site or infusion of the antisense nucleic acid into an ovary-associated body fluid. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

The invention also encompasses ribozymes. Ribozymes are catalytic RNA molecules with ribonuclease activity which are capable of cleaving a single-stranded nucleic acid, such as an mRNA, to which they have a complementary region. Thus, ribozymes can be used to catalytically cleave mRNA transcripts to thereby inhibit translation of the protein encoded by the mRNA. A ribozyme having specificity for a nucleic acid molecule encoding a polypeptide corresponding to a marker of the invention can be designed based upon the nucleotide sequence of a cDNA corresponding to the marker.

The invention also encompasses nucleic acid molecules which form triple helical structures. For example, expression of a polypeptide of the invention can be inhibited by targeting nucleotide sequences complementary to the regulatory region of the gene encoding the polypeptide (e.g., the promoter and/or enhancer) to form triple helical structures that prevent transcription of the gene in target cells.

The invention also encompasses the use of RNA interference or "RNAi" which is a term initially coined by Fire and co-workers to describe the observation that double-stranded RNA (dsRNA) can block gene expression when it is introduced into worms (Fire et al. (1998) Nature 391, 806-811). dsRNA directs gene-specific, post-transcriptional silencing in many organisms, including vertebrates, and has provided a new tool for studying gene function.

The phenomenon of RNA interference is described and discussed in Bass, Nature 411: 428-29 (2001); Elbashir et al., Nature 411: 494-98 (2001); and Fire et al., Nature 391: 806-11 (1998), where methods of making interfering RNA also are discussed. An "siRNA" or "RNAi" refers to a nucleic acid that forms a double stranded RNA, which double stranded RNA has the ability to reduce or inhibit expression of a gene or target gene when the siRNA expressed in the same cell as the gene or target gene. "siRNA" thus refers to the double stranded RNA formed by the complementary strands. The complementary portions of the siRNA that hybridize to form the double stranded molecule typically have substantial or complete identity. In one embodiment, an siRNA refers to a nucleic acid that has substantial or complete identity to a target gene and forms a double stranded siRNA. The sequence of the siRNA can correspond to the full-length target gene, or a subsequence thereof. Typically, the siRNA is at least about 15-50 nucleotides in length (e.g., each complementary sequence of the double stranded siRNA is 15-50 nucleotides in length, and the double stranded siRNA is 15-50 base pairs in length, preferable about preferably about 20-30 base nucleotides, preferably about 20-25 nucleotides in length, e.g., 20, 21, 22, 23, 24, 25, 26, 27, 28, 29, or 30 nucleotides in length.

In various embodiments, the nucleic acid molecules of the invention can be modified at the base moiety, sugar moiety or phosphate backbone to improve, e.g., the stability, hybridization, or solubility of the molecule. For example, the deoxyribose phosphate backbone of the nucleic acids can be modified to generate peptide nucleic acids. As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis.

PNAs can be used in therapeutic and diagnostic applications. For example, PNAs can be used as antisense or antigene agents for sequence-specific modulation of gene expression by, e.g., inducing transcription or translation arrest or inhibiting replication. PNAs can also be used, e.g., in the analysis of single base pair mutations in a gene by, e.g., PNA directed PCR clamping; as artificial restriction enzymes when used in combination with other enzymes.

In other embodiments, the oligonucleotide can include other appended groups such as peptides (e.g., for targeting host cell receptors in vivo), or agents facilitating transport across the cell membrane or the blood-brain barrier. In addition, oligonucleotides can be modified with hybridization-triggered cleavage agents or intercalating agents. The oligonucleotide can be conjugated to another molecule, e.g., a peptide, hybridization triggered cross-linking agent, transport agent, hybridization-triggered cleavage agent, etc.

The invention also includes molecular beacon nucleic acids having at least one region which is complementary to a nucleic acid of the invention, such that the molecular beacon is useful for quantitating the presence of the nucleic acid of the invention in a sample. A "molecular beacon" nucleic acid is a nucleic acid comprising a pair of complementary regions and having a fluorophore and a fluorescent quencher associated therewith. The fluorophore and quencher are associated with different portions of the nucleic acid in such an orientation that when the complementary regions are annealed with one another, fluorescence of the fluorophore is quenched by the quencher. When the complementary regions of the nucleic acid are not annealed with one another, fluorescence of the fluorophore is quenched to a lesser degree.

Microarrays

In another aspect, the present invention describes the use of high density oligonucleotide microarrays or solid supports or microbeads to measure in a standardized fashion PCR products following standardized quantitative RT-PCR according to the methods described herein, as shown in FIGS. 9a and 9b.

In certain embodiments, the preparation of high-density oligonucleotide arrays can be made with the following properties. For each gene, an oligonucleotide of any length that will bind with specificity to both the competitive template, CT, and native template, NT, is spotted of a filter. To identify a suitable oligonucleotide, the region between the forward primer (common to both the NT and CT) and the 3' 20 bp of the reverse CT primer is evaluated. An oligonucleotide with high melting temperature, preferably greater than about 70 degrees centigrade, and be attached to the solid support at a previously designated location In FIG. 9a the oligonucleotides specific to each gene are designated with different bars (open, slashed, or striped).

Then, the CT and NT PCR products, amplified according to the methods described above, are hybridized to the spots. Each gene (NT and CT) is amplified separately. Then the PCR products are pooled for hybridization to the membrane described above, and illustrated in FIG. 9a. The CT and NT PCR products appear as thin black curved lines in the FIG. 9a.

Two oligonucleotide probes, each labeled with a different fluor, are prepared for each gene. One oligonucleotide will be homologous to, and will bind to sequences unique to the NT for a gene that was PCR-amplified using the methods described herein. This oligonucleotide will bind to the region of the NT that is not homologous to the CT and will be labeled with a different fluor. The other oligonucleotide will be specific to the CT and will be labeled with a different fluor. It will be homologous to and will bind to CT sequences that span the 3' end of the reverse primer. The NT-specific and CT-specific oligonucleotides for multiple genes will be mixed in equal amounts and hybridized to the gene-specific PCR products bound to the gene-specific oligonucleotides spotted on the filter. The ratio between the fluors bound to the spot will quantify the NT relative to CT. The fluorescent tagged probe (shaded black) is specific to the NT and the fluorescent tagged probe (unshaded) is specific to the CT.

In this assay, although there may be different binding affinities between the CT and CT probe relative to that between the NT and NT probe, this difference will be consistent between different samples assessed, and from one experiment to another.

This method also works with other solid phase hybridization templates including, for example, microbeads, glass slides, or chips prepared by photolithography. No matter what template is used, the products of standardized RT-PCT, using the standardized mixture of competitive templates, will be the starting point, as shown with microbeads in FIG. 9b where microbeads gene specificity is conferred by the fluorescent color of the bead, rather than the location on the microarray.

Cisplatin

The examples set forth below relate to cis-Diamminedichloroplatinum (II), otherwise known as cisplatin, and related compounds. Cisplatin is a chemical compound within a family of platinum coordination complexes which are art-recognized as being a family of related compounds. Cisplatin was the first platinum compound shown to have anti-malignant properties. The language "platinum compounds" is intended to include cisplatin, compounds which are structurally similar to cisplatin, as well as analogs and derivatives of cisplatin. The language "platinum compounds" can also include "mimics". "Mimics" is intended to include compounds which may not be structurally similar to cisplatin but mimic the therapeutic activity of cisplatin or structurally related compounds in vivo.

The platinum compounds of this invention are those compounds which are useful for inhibiting tumor growth in subjects (patients). More than 1000 platinum-containing compounds have been synthesized and tested for therapeutic properties. One of these, carboplatin, has been approved for treatment of ovarian cancer. Both cisplatin and carboplatin are amenable to intravenous delivery. However, compounds of the invention can be formulated for therapeutic delivery by any number of strategies. The term platinum compounds also is intended to include pharmaceutically acceptable salts and related compounds. Platinum compounds have previously been described in U.S. Pat. Nos. 6,001,817, 5,945,122, 5,942,389, 5,922,689, 5,902,610, 5,866,617, 5,849,790, 5,824,346, 5,616,613, and 5,578,571, all of which are expressly incorporated by reference.

Cisplatin and related compounds are thought to enter cells through diffusion, whereupon the molecule likely undergoes metabolic processing to yield the active metabolite of the drug, which then reacts with nucleic acids and proteins. Cisplatin has biochemical properties similar to that of bifunctional alkylating agents, producing interstrand, intrastrand, and monofunctional adduct cross-linking with DNA.

Databases

The present invention includes relational numerically standardized databases containing sequence information, for instance for the genes of Tables 1 and 5, as well as gene expression information in various lung tissue samples. Databases may also contain information associated with a given sequence or tissue sample such as descriptive information about the gene associated with the sequence information, or descriptive information concerning the clinical status of the tissue sample, or the patient from which the sample was derived. The database may be designed to include different parts, for instance a sequences database and a gene expression database. Methods for the configuration and construction of such databases are widely available.

The numerically standardized databases of the invention may be linked to an outside or external database. In a preferred embodiment, as described in Tables 1-5, the external database is GenBank and the associated databases maintained by the National Center for Biotechnology Information (NCBI).

Any appropriate computer platform may be used to perform the necessary comparisons between sequence information, gene expression information and any other information in the database or provided as an input. For example, a large number of computer workstations are available from a variety of manufacturers, such has those available from Silicon Graphics. Client-server environments, database servers and networks are also widely available and appropriate platforms for the databases of the invention.

The databases of standardized numerical data of the invention may be used to produce, among other things, electronic Northerns to allow the user to determine the cell type or tissue in which a given gene is expressed and to allow determination of the abundance or expression level of a given gene in a particular tissue or cell.

The databases of the invention may also be used to present information identifying the expression level in a tissue or cell of a set of genes comprising at least one gene in Tables 1-5 comprising the step of comparing the expression level of at least one gene in Tables 1-5 in the tissue to the level of expression of the gene in the database. Such methods may be used to predict the physiological state of a given tissue by comparing the level of expression of a gene or genes in Tables 1-5 from a sample to the expression levels found in tissue from normal lung, malignant lung or NSCLC. Such methods may also be used in the drug or agent screening assays as described below.

Computer System

In another aspect, the present invention relates to a computer system comprising: (a) a database containing standardized numerical gene expression information identifying the expression level in lung tissue of a set of genes comprising at least two genes in Tables 1 and 5 or c-myc×E2F-a/p21; and (b) a user interface to view the information. The database can further include at least one or more of the following: sequence information for the genes; information identifying the expression level for the set of genes in normal lung tissue; information identifying the expression level of the set of genes in non small cell cancer tissue, records including descriptive information from an external database, which information correlates said genes to records in the external database; including, for example, where the external database is GenBank and information or specific characteristics of the cells or tissues or patients from which the were derived.

In another aspect, the present invention relates to a method of using the computer system described above to present information identifying the expression level in a tissue or cell of at least one gene in Tables 1 and 5, by comparing the expression level of at least one gene in Tables 1 and 5 in the tissue or cell to the level of expression of the gene in the database. In certain embodiments, the expression level of at least two, five, seven, and/or ten genes are compared.

In yet other aspects, the method further includes displaying the level of expression of at least one gene in the tissue or cell sample compared to the expression level in lung cancer.

Kits

The invention further includes kits combining, in different combinations, at least one of: high-density oligonucleotide arrays, reagents for use with the microarrays, reagents for StaRT-PCR amplification of the specified genes including gene specific primers and standardized mixtures of internal standards, signal detection and array-processing instruments, gene expression databases, and analysis and database management software described above. The kits may be used, for example, to predict or model the toxic response of a test compound, to monitor the progression of disease states, to identify genes that show promise as new drug targets and to screen known and newly designed drugs as discussed herein.

In certain embodiments, the kit includes at least one solid support, as described herein, packaged with gene expression information for said genes. In certain embodiments, the gene expression information comprises gene expression levels in a tissue or cell sample exposed to a toxin. Also, in certain embodiments, the gene expression information is in an electronic format, including, for example, the standardized gene expression database described herein.

The databases packaged with the kits are a compilation of expression patterns from human or laboratory animal genes and gene fragments (corresponding to the genes of Tables 1 and 5). Data is collected from a repository of both normal and diseased tissues and provides reproducible, quantitative results, i.e., the degree to which a gene is up-regulated or down-regulated under a given condition.

The kits are useful in the pharmaceutical industry, where the need for early drug testing is strong due to the high costs associated with drug development, but where bioinformatics, in particular gene expression informatics, is still lacking. These kits reduce the costs, time and risks associated with traditional new drug screening using cell cultures and laboratory animals. The results of large-scale drug screening of pre-grouped patient populations, pharmacogenomics testing, can also be applied to select drugs with greater efficacy and fewer side-effects. The kits may also be used by smaller biotechnology companies and research institutes who do not have the facilities for performing such large-scale testing themselves.

Databases and software designed for use with microarrays is discussed in Balaban et al., U.S. Pat. No. 6,229,911, a computer-implemented method for managing information, stored as indexed tables, collected from small or large numbers of microarrays, and U.S. Pat. No. 6,185,561, a computer-based method with data mining capability for collecting gene expression level data, adding additional attributes and reformatting the data to produce answers to various queries. Chee et al., U.S. Pat. No. 5,974,164, disclose a software-based method for identifying mutations in a nucleic acid sequence based on differences in probe fluorescence intensities between wild type and mutant sequences that hybridize to reference sequences.

Assays and Identification of Therapeutic and Drug Screening Targets

It should be understood that in certain preferred embodiments, the microarrays as described herein, and in particular, with reference to the example shown in FIGS. 9a and 9b, are especially useful. However, it should also be understood, that in certain other embodiments, other hybridization assay format may be used, including solution-based and solid support-based assay formats. Solid supports containing oligonucleotide probes for differentially expressed genes of the invention can be filters, polyvinyl chloride dishes, silicon or glass based chips, etc. Such wafers and hybridization methods are widely available. Any solid surface to which oligonucleotides can be bound, either directly or indirectly, either covalently or non-covalently, can be used. Examples of a solid support include a high density array or DNA chip. These contain a particular oligonucleotide probe in a predetermined location on the array. Each predetermined location may contain more than one molecule of the probe, but each molecule within the predetermined location has an identical sequence. Such predetermined locations are termed features. There may be, for example, about 2, 10, 100, 1000 to 10,000; 100,000 or 400,000 of such features on a single solid support. The solid support, or the area within which the probes are attached may be on the order of a square centimeter.

Oligonucleotide probe arrays for expression monitoring can be made and used according to any techniques known in the art. Such probe arrays may contain at least two or more oligonucleotides that are complementary to or hybridize to two or more of the genes described herein. Such arrays may also contain oligonucleotides that are complementary or hybridize to at least about 2, 3, 4, 5, 6, 7, 8, 9, 10, 20, 30, 50, 70, 100 or more the genes described herein.

Methods of forming high density arrays of oligonucleotides with a minimal number of synthetic steps are known. The oligonucleotide analogue array can be synthesized on a solid substrate by a variety of methods, including, but not limited to, light-directed chemical coupling, and mechanically directed coupling. In brief, the light-directed combinatorial synthesis of oligonucleotide arrays on a glass surface proceeds using automated phosphoramidite chemistry and chip masking techniques. In one specific implementation, a glass surface is derivatized with a silane reagent containing a functional group, e.g., a hydroxyl or amine group blocked by a photolabile protecting group. Photolysis through a photolithogaphic mask is used selectively to expose functional groups which are then ready to react with incoming 5' photoprotected nucleoside phosphoramidites. The phosphoramidites react only with those sites which are illuminated (and thus exposed by removal of the photolabile blocking group). Thus, the phosphoramidites only add to those areas selectively exposed from the preceding step. These steps are repeated until the desired array of sequences have been synthesized on the solid surface. Combinatorial synthesis of different oligonucleotide analogues at different locations on the array is determined by the pattern of illumination during synthesis and the order of addition of coupling reagents.

In addition to the foregoing, additional methods can be used to generate an array of oligonucleotides on a single substrate. High density nucleic acid arrays can also be fabricated by depositing premade or natural nucleic acids in predetermined positions. Synthesized or natural nucleic acids are deposited on specific locations of a substrate by light directed targeting and oligonucleotide directed targeting. Another embodiment uses a dispenser that moves from region to region to deposit nucleic acids in specific spots.

Determination of IGEI

A sample of cancerous cells with unknown sensitivity to a given drug is obtained from a patient. An expression level is measured in the sample for a gene corresponding to one of the nucleotide sequences claimed herein as a (IGEI) marker set. The expression level of the marker in the sample is compared with the expression level of the marker measured previously in cells with known drug sensitivity. If the expression level of the marker in the sample is most similar to the expression levels of the marker in cells with low sensitivity to the given drug, then low sensitivity to that drug is predicted for the sample. If the expression level of the marker in the sample is most similar to the expression levels of the marker in cells with medium sensitivity to the given drug, then medium sensitivity to that drug is predicted for the sample. If the expression level is most similar to the expression levels of the marker in cells with high sensitivity to the given drug, then high sensitivity to that drug is predicted for the sample.

Thus, by examining the expression of one or more of the identified markers in a sample of cancer cells, it is possible to determine which therapeutic agent(s), or combination of agents, to use as the appropriate treatment agents.

By examining the expression of one or more of the identified markers in a sample of cancer cells taken from a patient during the course of therapeutic treatment, it is also possible to determine whether the therapeutic agent is continuing to work or whether the cancer has become resistant (refractory) to the treatment protocol. These determinations can be made on a patient-by-patient basis or on an agent by agent (or combinations of agents). Thus, one can determine whether or not a particular therapeutic treatment is likely to benefit a particular patient or group/class of patients, or whether a particular treatment should be continued.

The identified (IGEI) marker sets further provide previously unknown or unrecognized targets for the development of anti-cancer agents, such as chemotherapeutic compounds, and can be used as targets in developing single agent treatment as well as combinations of agents for the treatment of cancer.

EXAMPLES

A skilled artisan can readily recognize that there is no limit as to the structural nature of the agents of the present invention. As such, without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

In one embodiment, standardized RT (StaRT)-PCR, was employed to assess various mutidrug resistant genes in a set of non-small cell lung cancer (NSCLC) cell lines with a previously determined range of sensitivity to cisplatin. Data were obtained in the form of target gene molecules relative to $10^6$ β-actin (ACTB) molecules. To cancel the effect of ACTB variation among the different ells lines individual gene expression values were incorporated into ratios of one gene to another. Each two-gene ratio was compared as a single variable to chemoresistance for each of eight NSCLC cell lines using multiple regression. Following validation, single variable models best correlated with chemoresistance (p<0.001), were determined. In certain embodiments, the variable models included: ERCC2/XPC, ABCC5/GTF2H2, ERCC2/GTF2H2, XPA/XPC and XRCC1/XPC. All single variable models were examined hierarchically to achieve two variable models. The two-variable model with the highest correlation was (ABCC5/GTF2H2, ERCC2/GTF2H2) with an $R^2$ value of 0.96 (p<0.001). In certain embodiments, these markers are suitable for assessment of small samples of tissue such as fine needle aspirate biopsies to prospectively identify cisplatin resistant tumors.

StaRT-PCR is used to measure expression of 35 genes involved in DNA repair, multi-drug resistance, cell cycling and apoptosis in two cell lines previously reported to be the least (H460) and most (H1435) chemoresistant among 20 NSCLC cell lines. Weaver, D. A., Zahorchak, R., Varnavas, L., Crawford, E. L., Warner, K. A., Willey, J. C., Comparison of expression patterns by microarray and standardized RT-PCR analyses in lung cancer cell lines with varied sensitivity to carboplatin, Proc Am Assoc Cancer Res (2001) abstract, 42, 606. Tsai, C. M., Chang, K. T., Wu, L. H., Chen, J, Y., Gazdar, A. F., Mitsudomi, T., Chen, M. H., Perng, R. P., Correlations between intrinsic chemoresistance and HER-2/neu gene expression, p53 mutations, and cell proliferation characteristics in non-small cell lung cancer cell lines, Cancer Res (1996), 56, 206-109. Genes involved in DNA repair (ERCC2, XRCC1) and drug influx/efflux (ABCC5) are associated with chemoresistance. The number of genes from each of these two categories was expanded to include additional representative genes associated with generalized DNA damage recognition and repair (DDIT3), associated specifically with NER (LIG1, ERCC3, GTF2H2, XPA, XPC), or associated with drug transport (ABCC1, ABCC4, ABCC10). Expression of these twelve genes was measured in eight NSCCLC cell lines with variable cisplatin resistance. Tsai, C. M., Chang, K. T., Wu, L. H., Chen, J, Y., Gazdar, A. F., Mitsudomi, T., Chen, M. H., Perng, R. P., Correlations between intrinsic chemoresistance and HER-2/neu gene expression, p53 mutations, and cell proliferation characteristics in non-small cell lung cancer cell lines, Cancer Res (1996), 56, 206-109. StaRT-PCR data were obtained using ACTB as a reference gene. Thus, data were reported in the form of mRNA molecules/$10^6$ ACTB molecules. These data then were combined into interactive gene expression indices (IGEI) by placing one or more genes directly associated with the phenotype on the numerator and one or more genes negatively associated with the phenotype on the denominator using the quantitative reverse transcriptase-PCR method described in the Willey U.S. Pat. Nos. 5,639,606; 5,643,765; and 5,876,978. Willey, J. C., Crawford, E. L., Jackson, C. M., Weaver, D. A., Hoban, J. C., Khuder, S. A., DeMuth, J. P., Expression measurement of many genes simultaneously by quantitative RT-PCR using standardized mixtures of competitive templates, Am J Respir Cell Mol Biol (1998), 19, 6-17. DeMuth, J. P., Jackson, C. M., Weaver, D. A., Crawford, E. L., Durzinsky, D. S., Durham, S. J., Zaher, A., Philips, E. R., Khuder, S. A., Willey, J. C., The gene expression index c-myc×E2F1/p21 is highly predictive of malignant phenotype in human bronchial epithelial cells, Am J Respir Cell Mol Biol (1998), 19, 18-24. The IGEI are geter predictors of phenotypes than are the expression levels of individual genes. For certain cancer-related phenotypes. Willey, J. C., Crawford, E. L., Jackson, C. M., Weaver, D. A., Hoban, J. C., Khuder, S. A., DeMuth, J. P., Expression measurement of many genes simultaneously by quantitative RT-PCR using standardized mixtures of competitive templates, Am J Respir Cell Mol Biol (1998), 19, 6-17. DeMuth, J. P., Jackson, C. M., Weaver, D. A., Crawford, E. L., Durzinsky, D. S., Durham, S. J., Zaher, A., Philips, E. R., Khuder, S. A., Willey, J. C., The gene expression index c-myc×E2F1/p21 is highly predictive of malignant phenotype in human bronchial epithelial cells, Am J Respir Cell Mol Biol (1998), 19, 18-24. Crawford, E. L., Khuder, S. A., Durham, S. J., Frampton, M., Utell, M., Thilly, W. G., Weaver, D. A., Ferencak, W. J., Jennings, C. A., Hammersley, J. R., Olson, D. A., Willey, J. C., Normal bronchial epithelial cell expression of glutathione transferase P1, glutathione transferase M3, and glutathione peroxidase is low in subjects with bronchogenic carcinoma, Cancer Res (2000), 60, 1609-1618. Rots, J. G., Willey, J. C., Jansen, G., Van Zantwijk, C. H., Noordhuis, P., DeMuth, J. P., Kuiper, E., Verrman, A. J., Pieters, R., Peters, G. J., mRNA expression levels of methotrexate resistance-related proteins in childhood leukemia as determined by a standardized competitive template-based RT-PCR method, Leukemia (2000), 14, 2166-2175. A further advantage of IGEI is that they control for previously observed variation in the reference gene value (in this case, ACTB) from one cell line to another. Willey, J. C., Crawford, E. L., Jackson, C. M., Weaver, D. A., Hoban, J. C., Khuder, S. A., DeMuth, J. P., Expression measurement of many genes simultaneously by quantitative RT-PCR using standardized mixtures of competitive templates, Am J Respir Cell Mol Biol (1998), 19, 6-17. DeMuth, J. P., Jackson, C. M., Weaver, D. A., Crawford, E. L., Durzinsky, D. S., Durham, S. J., Zaher, A., Philips, E. R., Khuder, S. A., Willey, J. C., The gene expression index c-myc×E2F1/p21 is highly predictive of malignant phenotype in human bronchial epithelial cells, Am J Respir Cell Mol Biol (1998), 19, 18-24. When a single gene in the numerator is divided by another single gene in the denominator, the reference value mathematically cancels out. The IGEI values were compared to cisplatin chemoresistance among the eight NSCLC cell lines with variable resistance. Results then were validated in an additional six NSCLC cell lines.

Example I

Materials and Methods

Cell Culture

Non-small cell lung cancer (NSLC) cell lines H460, H1155, H23, H838, H1334, H1437, H1355, H1435, H358, H322, H441, H522, H226 and H647 were obtained from the American Type Culture Collection (Rockville, Md.). All cells were incubated in RPMI-1640 medium (Biofluids, Inc., Rockville, Md.) containing 10% fetal bovine serum (FBS) and 1 mM glutamine at 37° C. in the presence of 5% $CO_2$. Proliferative, subconfluent cultures were obtained from RNA extractions and subsequent analyses.

Reagents

10×PCR buffer for the Rapidcycler (500 mM Tris, pH 8.3; 2.5 mg/µl BSA; 30 mM $MgCl_2$) was obtained from Idaho Technology, Inc. (Idaho Falls, Id.). Taq polymerase (5 U/µl), oligo dT primers, RNasin (25 U/µl) and dNTPs were obtained from Promega (Madison, Wis.). M-MLV reverse transcriptase (200 U/µl) and 5× first strand buffer (250 mM Tris-HCl, pH 8.3; 375 mM KCl; 15 mM $MgCl_2$—; 50 mM DTT) were obtained from Gibco BRL (Gaithersburg, Md.). DNA 7500 Assay kits containing dye, matrix and standards were obtained from Agilent Technologies, Inc. (Palo Alto, Calif.). All other chemicals and reagents were molecular biology grade.

RNA Extraction and Reverse Transcription

Total RNA was isolated from cell cultures by a TriReagent protocol (Molecular Research Center, Inc., Cincinnati, Ohio). Chomczynski, P., A reagent for the single-step simultaneous isolation of RNA, DNA and proteins from cell and tissue samples, Biotechniques (1993), 15, 536-537. Following extraction, approximately 1 µg of total RNA for each cell line was reverse-transcribed using M-MLV reverse-transcriptase and an oligo dT primer as previously described in Willey, J. C., Coy, E., Brolly, C., Utell, M. J., Frampton, M. W., Hammersley, J., Thilly, W. G., Olson, D., Cairns, K., Xenobiotic metabolism enzyme gene expression in human bronchial epithelial and alveolar macrophage cells, Am. J. Respir. Cell Biol. (1996), 14, 262-271.

Quantitative Standardized RT (StaRT)-PCR

Gene expression was determined using quantitative StaRT-PCR protocols described in U.S. Pat. Nos. 5,639,606; 5,643,765; and 5,876,978 and in Willey, J. C., Crawford, E. L., Jackson, C. M., Weaver, D. A., Hoban, J. C., Khuder, S. A., DeMuth, J. P., Expression measurement of many genes simultaneously by quantitative RT-PCR using standardized mixtures of competitive templates, Am J Respir Cell Mol Biol (1998), 19, 6-17. Willey, J. C., Coy, E., Brolly, C., Utell, M. J., Frampton, M. W., Hammersley, J., Thilly, W. G., Olson, D., Cairns, K, Xenobiotic metabolism enzyme gene expression in human bronchial epithelial and alveolar macrophage cells, Am J Respir Cell Mol Biol (1996), 14, 262-271. Apostolakos, M. J., Schuermann, W. H., Frampton, M. W., Utell, M. J., Willey, J. C., Measurement of gene expression by multiplex competitive polymerase chain reaction, Anal. Biochem. (1993), 213, 277-284. Willey, J. C., Coy, E. L. Frampton, M. W., Torres, A., Apostolakos, M. J., Hoehn G., Schuermann, W. H. Thilly W. G., Olson, D. E., Hammersley, J. R., Crepsi, C. L. Utell, M. J., Quantitative RT-PCR measurement of cytochromes p4a50 1A1, 1B1, and 2B7, microsomal epoxide hydrolase, and NADPH oxidereductase expression in lung cells of smokers and non-smokers. Am. J. Respir. Cell Mol. Biol. (1997) 17, 114-124. Briefly, a master mixture containing buffer, $MgCl_2$, dNTPs, sample cDNA, Taq polymerase and competitive template (CT) mixture was prepared and 9 µl aliquots dispensed into 0.6 ml microfuge tubes containing 1 µl of gene-specific primers. The CT mixture comprises gene-specific internal standard competitive templates (CTs) at defined concentrations relative to one another and also contains CT for a housekeeping gene, ACTB, to allow for the normalization of all specific gene data. All primers used for PCT and those used in the construction of the CTs, are listed in Table 1. PCR reactions were subjected to 35 cycles of PCR with 5 seconds of denaturation at 94° C., 10 seconds of annealing at 58° C. and 15 seconds of elongation at 72° C. in a Rapidcycler (Idaho Technology, Inc.). PCR products were electrophoretically separated and quantified in an Agilent 2100 Bioanalyzer (Agilent Technologies, Inc.) with the DNA 7500 Assay Kit.

Chemoresistance of NSCLC Cell Lines

Chemoresistance $IC_{50}$ (µm) values of the NSCLC cell lines used for several chemotherapeutic agents were previously determined, as described in Tsai, C. M., Chang, K. T., Wu, L. H., Chen, J, Y., Gazdar, A. F., Mitsudomi, T., Chen, M. H., Perng, R. P., Correlations between intrinsic chemoresistance and HER-2/neu gene expression, p53 mutations, and cell proliferation characteristics in non-small cell lung cancer cell lines, Cancer Res (1996), 56, 206-109 and are summarized for cisplatin in Table 2.

Statistical Analyses

Ratios of one gene to another, from each of the initial eight NSCLC cell lines, were subjected to multiple regression analysis with SAS (version 6, $4^{th}$ edition, volume 2) statistical package (SAS Institute Inc., Cary, N.C.) to determine the combination of genes that best predict cisplatin resistance. Each ratio was compared separately to chemoresistance and ratios with significant correlation to resistance ($R^2 \geq 0.88$, $p<0.001$) then were examined hierarchically to achieve two variable models based on the highest $R^2$ values. Following assessment of an additional 6 cell lines, results for all 14 NSCLC cell lines were combined and subjected to analysis as described.

Results: Reproducibility

Among the gene expression measurements for which three or more replicate values were obtained, the mean coefficient of variation was 38.5% (raw data available at website). This is similar to the reproducibility observed in other gene expression studies using the StaRT-PCR method. Willey, J. C., Crawford, E. L., Jackson, C. M., Weaver, D. A., Hoban, J. C., Khuder, S. A., DeMuth, J. P., Expression measurement of many genes simultaneously by quantitative RT-PCR using standardized mixtures of competitive templates, Am. J. Respir. Cell Mol. Biol. (1998), 19, 6-17. Crawford, E. L., Khuder, S. A., Durham, S. J., Frampton, M., Utell, M., Thilly, W. G., Weaver, D. A., Ferencak, W. J., Jennings, C. A., Hammersley, J. R., Olson, D. A., Willey, J. C., Normal bronchial epithelial cell expression of glutathione transferase P1, glutathione transferase M3, and glutathione peroxidase is low in subjects with bronchogenic carcinoma, Cancer Res. (2000), 60, 1609-1618.

Individual Gene Expression Measurements and Chemoresistance

The results of the direct comparison of individual gene expression mean values versus cisplatin chemoresistance for the first set of eight cell lines (Group 1) are presented in Table 3. All StaRT-PCR data values were in the form of molecules/$10^6$ ACTB molecules. For 8/12 genes assessed, there was significant ($p<0.05$) correlation.

Establishment of Inter-Active Gene Expression Ratios

IGEI were established comprising every possible combination of the expression value of one gene divided by the expression value of another gene for data obtained from each of the initial eight NSCLC cell lines (Group 1). Each expression value was calculated as molecules/$10^6$ ACTB molecules. Thus, in these IGEI the effect of the reference gene, ACTB, is cancelled. For Example:

ERCC2 molecules/$10^6$ ACTB molecules÷XPC molecules/$10^6$ ACTB molecules=ERCC2 molecules/XPC molecules.

Bivariate analysis of each two-gene ratio versus corresponding cisplatin $IC_{50}$ chemoresistance values was conducted among the eight cell lines (Table 4). There were 12 genes assessed and 11 sets of ratios for each gene resulting in 132 ratios. The sets of 11 ratios for each gene then were organized in descending order such that the ratio set listed first was that for which the average correlation with chemoresistance was highest, and the ratio set listed last was that for which the average correlation with chemoresistance was lowest. Thus the ratio set with ERCC2 in the numerator is listed first because the average of the r values for the ratios between ERCC2 and each of the other eleven genes was the most positive among the twelve genes evaluated. In contrast, the ratio set with XPC in the numerator is listed last because the ratios between XPC and each of the other 11 genes had the most negative correlation with chemoresistance.

Modeling of Gene Expression with Chemoresistance

The ratios ERCC2/XPC, ABCC5/GTF2H2, ERCC2/XRCC1, ERCC2/GTF2H2, XPA/XPC, XRCC1/XPC, and ABCC5/XPC were the best single variable models (i.e., those with $R^2>0.87$) identified in the initial eight NSCLC cell lines by simple linear regression (Table 5). The effect of adding a second variable into the model was then assessed. The best two variable model was (ABCC5/GTF2H2, ERCC2/GTF2H2) with an $R^2$ value of 0.96.

Validation of Models

These single and two variable models were tested in an additional six NSCLC cell lines. From the statistical analysis of the combined data for all 14 NSCLC cell lines, the p value improved or stayed the same for three of the single variable models (ERCC2 1 XPC, ABCC5/GTF2H2, XRCC1/XPC), as well as the two variable model. The decline in p value for ERCC2/GTF2H2 and XPA/XPC was small and not significant. In contrast, ERCC2/XRCC1 was no longer significantly associated with chemoresistance, and the p value declined substantially for ABCC5/XPC.

Analysis of Results

The results obtained by measuring gene expression with StaRT-PCR, incorporating values for individual genes into IGEI, and correlating IGEI with chemoresistance provides several models useful as predictors of cisplatin chemoresistance in cultured NSCLC cells. These models comprise genes associated with cisplatin chemoresistance, including ABCC5, ERCC2, XPA, and XRCC1. Increased expression of ABCC5, also known as MRP5, is associated with exposure to platinum drugs in lung cancer in vivo and/or the chronic stress response to xenobiotics. Thus, increased resistance to platinum drugs with increased ABCC5 levels may be due to glutathione S-platinum complex efflux.

The remaining genes directly associated with chemoresistance, XPA and ERCC2, are components of the nucleotide excision repair (NER) mechanism which generally is recognized as the major repair response to DNA damage induced by chemotherapeutic agents such as cisplatin. In NER, XPA is the main DNA lesion recognition protein (Asahina, H., Kuraoka, I., Shirakawa, M., Morita, E. H., Miura, N., Miyamoto, I., Ohtsuka, E., Okada, Y., Tanaka, K., The XPA protein is a zinc metalloprotein with an ability to recognize various kinds of DNA damage, Mutat. Res. DNA Repair (1994), 315, 229-237) and is the key element in assembly of the NER complex by recruiting several other proteins to the lesion site. Li, L., Peterson, C. A., Lu, X., Legerski, R. J., Mutations in XPA that prevent association with ERCC1 are defective in nucleotide excision repair, Mol Cell Biol (1995), 15, 1993-1998. Enhanced NER gene expression has been shown to be a major cause of resistance to cisplatin and other DNA-damaging chemotherapeutic agents (Zamble, D. B., Lippard, S. J., Cisplatin and DNA repair in cancer chemotherapy, Trends Biochem. Sci. (1995), 20, 435-439, Reed, E., Anticancer drugs: platinum analogs. In: Cancer: Principles and Practice of Oncology, (1993), 390-399. Editors V. T. Devita, Jr., S. Hellman and S. A. Rosenberg, Lippincott, Philadelphia) and overexpression of the XPA gene component of NER has been associated with resistance to cisplatin in human ovarian cancer. Dabholkar, M., Vionnet, J., Bostick-Bruton, F., Yu, J. J., Reed, E., Messenger RNA levels of XPAC and ERCC1 in ovarian cancer tissue correlate with response to platinum-based chemotherapy, J. Clin. Invest. (1994), 94, 703-708. ERCC2 specifically is a component of the transcription factor IIH (TFIIH) which consists of seven polypeptides (Mu, D., Park, C. H., Matsunaga, T., Hsu, D. S., Reardon, J. T., Sancar, A., Reconstitution of human DNA repair excision nuclease in a highly defined system, J. Biol. Chem. (1995), 270, 2415-2418, Mu, D., Hus, D. S., Sancar, A., Reaction mechanism of human DNA repair excision nuclease, J. Biol. Chem. (1996), 271, 8285-8294) and in its entirety is a repair factor. Schaeffer, L., Moncollin, V., Roy, R., Staub, A., Mezzina, M., Sarasin, A., Weeda, G., Hoeijmakers, J. H., Egly, J. M., The ERCC2/DNA repair protein is associated with the class II BTF2/TFIIH transcription factor, EMBO J (1994), 13, 2388-2392, Drapkin, R., Reardon, J. T., Ansari, A., Huang, J. C., Zawel, L., Ahn, K., Sancar, A., Reinberg, D., Dual role of TFIIH in DNA excision repair and in transcription by RNA polymerase II, Nature (1994), 368, 769-772, Wang, Z., Svejstrup, J. Q., Feaver, W. J., Wu, X., Kornberg, R. D., Friedberg, E. C., Transcription factor b (TFIIH) is required during nucleotide-excision repair in yeast, Nature (1994), 368, 74-76. In NER, ERCC2 (or XPD) is essential for TFIIH helicase activity (Prakash, S., Sung, P., Prakash, L., DNA repair genes and proteins of *Saccharoyces cerevisiae*, Annu. Rev. Genet. (1993), 27, 33-70), and it has been demonstrated more recently that ERCC2 interacts specifically with GTF2H2 (or p44) and this interaction results in the stimulation of the 5' to 3' helicase activity. Coin, F., Marinoni, J. C., Rodoflo, C., Fribourg, S., Pedrinin, A. M., Egly, J. M., Mutations in the XPD helicase gene result in XP and TTD phenotypes, preventing interaction between XPD and the p44 subunit of TFIIH, Nature Genet, 20, 184-188.

With microarray analysis, because thousands of genes are assessed simultaneously, an index of all genes measured provides a stable reference for the amount of sample loaded from one microarray to another. In quantitative RT-PCR studies, typically, a single non-regulated gene is used as a loading reference, such as ACTB, GAPDH, cyclophilin or ribosomal RNA. However, all of these genes have been reported to vary among multiple samples. One way to assess inter-sample variation in reference gene expression among multiple samples is to compare variation between two reference genes. β-actin and GAPDH vary 50-fold relative to each other among bronchial epithelial cells (BEC) and even more between BEC and other cell types. Willey, J. C., Crawford, E. L., Jackson, C. M., Weaver, D. A., Hoban, J. C., Khuder, S. A., DeMuth, J. P., Expression measurement of many genes simultaneously by quantitative RT-PCR using standardized mixtures of competitive templates, Am. J. Respir. Cell Mol Biol. (1998), 19, 6-17. Rots, J. G., Willey, J. C., Jansen, G., Van Zantwijk, C. H., Noordhuis, P., DeMuth, J. P., Kuiper, E., Verrman, A. J., Pieters, R., Peters, G. J., mRNA expression levels of methotrexate resistance-related proteins in childhood leukemia as determined by a standardized competitive template-based RT-PCR method, Leukemia (2000), 14, 2166-2175. In situations where limited numbers of genes are measured (<200), an index of all genes for the normalization of data is not sufficiently stable. In order to eliminate the effect of unknown variation in the reference gene expression among samples, balanced ratios of one gene expression value obtained by StaRT-PCR to another were analyzed. These balanced ratios did not represent actual cellular concentration changes of the individual genes comprising the ratio, but related the expression of gene to another and are used for comparison with phenotypic determinants such as chemoresistance. In this study, IGEI analysis (Table 5) confirmed most of the results obtained by analysis of individual gene expression values relative to chemoresistance (Table 3). Specifically, XPC was the most stable of the twelve genes assessed relative to chemoresistance and the same eight genes were correlated with chemoresistance using XPC as the denominator (Table 4) as was the case using β-actin as the denominator (Table 3). Thus, variation in β-actin among this group of cDNA samples was not significant. In certain embodiments, it is useful to use IGEI to remove doubt regarding potential effect of variation in reference gene expression whenever possible.

As is presented in Table 4, by evaluating an empirically derived set of balanced ratios (IGEI) derived from expression values for all of the genes measured, it is possible to establish a hierarchy regarding the strength of association between a set of genes and a phenotype. Further, bivariate correlation of each gene relative to each of the others markedly increases the power of the analysis and helps to identify potential outliers that require further validation. In the example herein, the most obvious outlier is the high correlation between ERCC2/XRCC1 and chemoresistance. This is an outlier because (a) the sets of ratios with ERCC2 or XRCC1 in the numerator had the highest and fourth highest range r values respectively (Table 4), yet (b) all of the other ratios with ERCC2 in the numerator that had high r values had genes from the bottom of Table 4 in the denominator (i.e. XPC, GTF2H2, ABCC10, ERCC3, and Lig1 all were among the lowest in the table). Consistent with the evidence that ERCC2/XRCC1 is an outlier, when the Group 2 cell lines were evaluated, ERCC2/XRCC1 was no longer significantly associated with chemoresistance (Table 5). These findings provide further evidence for the value of measuring gene expression in standard, numerical format.

Thus, the association of ERCC2, ABCC5, XPA, and XRCC1 with chemoresistance is established through a sequential process involving (a) a first round of screening genes representing many different functional classes, (b) evaluating an expanded group of genes represented by those that are positively associated in the first round, (c) combining the positively connected data into interactive gene expression indices (IGEI), (d) using IGEI analysis to identify outliers, (e) building a model and (f) validating the data.

The method of the present invention highlights the necessity to evaluate the interaction of more than one gene involved in cisplatin chemoresistance and the interaction of multiple pathways that may give rise to chemoresistance.

Example II

The identification of many genes and their association to specific phenotypes will most likely lead to molecular cancer classification (Venter, J. C. The sequence of the human genome, Science, 291:1304-1351 (2001), Lander, E. S., Initial sequencing and analysis of the human genome, Nature, 409:860-921 (2001). This novel classification system has important clinical implications and may greatly improve patient care. Specifically, recognition of certain genotypes with associated phenotypes may reveal individual prognostic markers, chemosensitivity traits, and predict patient outcome. Molecular classification of lung cancer may greatly enhance cytologic diagnosis. Lung cancer is still primarily diagnosed using histopathological criteria. The heterogeneity of lung tumors often leads to inconsistent diagnosis (Sorenson, J. B., Hirsch, F. R., Gazdar, A., and Olsen, J. E., Cancer, 71:2971-2976, 1993), including difficulty distinguishing malignant from normal and metastatic lung tumors from primary tumors (Shirakusa, T., Tsutsui, M., Motomaga, R. Ando, K. and Kusano T., A. Surg., 54:655-658, 1966; Fling, A. and Lloyd, R. V., Arch. Pathol. Lab. Med. 166: 39-42, 1992).

Gene expression patterns have clarified clinical outcomes in lung and breast cancer patients. Garber et al., Proc. Natl. Acad. Sci. 98: 13874-113789 (2001) reported gene expression profiles of lung tumors correlated with transitional morphological classification. In addition, based on gene expression patterns, adenocarcinomas were further divided into 3 subtypes that differed significantly in patient survival. Bhattacharjee et al., Proc. Natl. Acad. Sci., 98: 13799990-13795 (2001) reported similar results. Lung adenocarcinomas were grouped into 4 subclasses based on gene expression patterns, and patients had statistically significant differences in survival. They also identified three metastatic lung tumors based on gene expression profile that were morphologically identified as primary lung tumors. Molecular classification of breast cancer tumors based on gene expression profiles and correlation to patient outcome and cell proliferation rates have also been reported in cases of hereditary breast cancer, sporadic breast cancer and human mannary epithelial cells (Hendenfalk, et al., New Eng. J. of Med. 344: 539-548, 2001; Sorlie et al., Proc. Natl. Acad. Sci. 98:10869-10874, 2001; and Perou et al., Distinctive gene expression patterns in human mammary epithelial cells and breast cancers Proc. Natl. Acad. Sci. USA vol. 96, no. 16: 9212-9217, 1999).

Most lung cancers are diagnosed primarily by fine-needle aspirate (FNA) biopsy tissues, pleural fluid samples and brushings of bronchial epithelial cells. These small, non-renewable tissue samples are challenging to use in gene expression studies. Microarray methods are appropriate for screening thousands of genes potentially involved in numerous cancer phenotypes, however they are unsuitable for FNA gene expression analysis because of large initial RNA amounts required, lack of internal standards, cost and time (Tyagi, S. and Kramer, F. R., Nature Biotech. 14: 303-308, 1996; DeRisi, J. L., Science, 278: 6860-6866, 1997). After target gene identification, gene expression analysis should be further evaluated with a quantitative, standardized gene expression method.

StaRT-PCR (Standardized Reverse Transcriptase-Polymerase Chain Reaction) is an ideal gene expression method to use in small clinical samples. It is useful to measure hundreds of genes simultaneously, requires small amounts of RNA, uses inexpensive equipment, is sensitive, standardized and highly reproducible (Willey et al., AM. J. Respir. Cell Mol. Biol. 19: 6-17, 1998, Crawford et al., Crawford, E. L., Godfridus, J. Peters, Noordhuis, P., Rots, M. G., Vondracek, M., Grafstrom, R. C., Lieuallen, K., Lennon, G., Zahorchak, R. J., Georgeson, M. J., Wali, A., Lechner, J. F., Fan, P-S., Kahaleh, B., Khuder, S. A., Warner, K. A., Weaver, D. A., and Willey, J. C. (2001), Reproducible gene expression measurement among multiple laboratories obtained in a blinded study using standardized RT (StaRT)-PCR, Molecular Diagnosis 6: 217-225, 2001). It is likely that malignant, chemoresistant and metastatic phenotypes result from the interactive effects of many genes. Because the data are numerical in StaRT-PCR studies, phenotypes can be represented by interactive gene expression indicies (IGEI). Demuth et al., Am. J. Respir. Cell Mol. Biol. 19: 18-24, 1998, reported the gene expression index of c-myc×E2F-1/p21 predicted malignancy in human bronchial epithelial cells better than any individual gene measured. In a similar study, the gene expression index of mGST× GSTM3×GSHP$_x$×GSHP$_x$A×GSTP1 was sensitive (90%) and 76% specific for detecting normal bronchogenic epithelial cells from subjects with bronchogenic carcinoma (Crawford et al., Cancer Research, 60: 1609-1618, 2000). Specifically, this interactive gene expression index identified individuals at risk for developing bronchogenic carcinoma better than any single gene.

The inclusion of standardized, competitive templates in every StaRT-PCR reaction allows direct intra-laboratory and inter-laboratory data comparison (Willey et al., 1998). Crawford et al., (2001) reported high inter-laboratory reproducibility using StaRT-PCR. (Crawford, E. L., Godfridus, J. Peters, Noordhuis, P., Rots, M. G., Vondracek, M., Grafstrom, R. C., Lieuallen, K., Lennon, G., Zahorchak, R. J., Georgeson, M. J., Wali, A., Lechner, J. F., Fan, P-S., Kahaleh, B., Khuder, S. A., Warner, K. A., Weaver, D. A., and Willey, J. C. (2001), Reproducible gene expression measurement among multiple laboratories obtained in a blinded study using standardized RT (StaRT)-PCR, Molecular Diagnosis 6:217-225, 2001). The generation of standardized, numerical data is needed for establishing a common, multi-institutional database. A recent modification of StaRT-PCR, termed multiplex standardized RT-PCR, allows further reduction in the amount of starting material needed for gene expression studies (Crawford, E. L., Warner, K. A., Khuder, S. A., Zahorchak, R. J., and Willey, J. C., Multiplex standardized RT-PCR for expression analysis of many genes in small clinical samples, Biochemical and biophysical Research Communications, 293: 509-516, 2002). Using multiplex StaRT-PCR at least 96 may be simultaneously evaluate using the same amount of cDNA that is normally used for measurement of one gene. (Crawford, et al. 2002, supra). This method was used to simultaneously measure 18 genes putatively associated with chemoresistance in a bronchogenic carcinoma sample obtained by FNA.

This example determines if a high c-myc×E2F-1/p21 gene expression index could augment cytopathological diagnosis of bronchogenic carcinoma. Standardized gene expression values for c-myc, E2F-1 and p21 and the interactive gene malignancy index were determined for eight primary lung FNA samples.

Materials and Methods

Cell Culture

The H1155 human NSCLC cell line was purchased from ATCC (Manassas, Va.), and cultured (37° C., 5.0% CO2) in RPMI supplemented with gentamicin (0.1%) (Biofluids, Rockville, Md.) and 10% fetal bovine serum (FBS) (Sigma, St. Louis, Mo.).

Evaluation of RNA Preservation, Extraction and Reverse Transcription

H1155 cells (1.0 E6) were placed in Preservcyt (CYTYC/ Boxborough, Mass.), RNA-Later (Ambion/Austin, Tex.) or TriReagent (Molecular Research Center, Cincinnati, Ohio) prior to RNA extraction. Time points and temperatures evaluated for RNA quality were 1, 3, 10 and 30 days and room temperature, 4° C. and −20° C. RNA was extracted from cells using Tri Reagent according to manufacturer's protocol. After extraction, RNA quality was evaluated on an Agilent 2100 Bioanalyzer for detection of 18s and 28s ribosomal peaks. mRNA samples were reverse transcribed using M-MLV reverse transcriptase (Gibco BRL, Gaithersburg, Md.) and oligo (dT) primer (Promega, Madison, Wis.) as previously described. (DeMuth, J. P., Jackson, C. M., Weaver, D. A., Crawford, E. L., Durzinsky, D. S., Durham, S. J., Zaher, A., Phillips, E. R., Khuder, S. A. and Willey, J. C. (1998), The gene expression index of c-myc×E2F-1/p21 is highly predictive of malignant phenotype in human bronchial epithelial cells, Am. J. Respir. Cell Mol. Biol., 19, 18-24. Crawford, E. L., Khuder, S. A., Durham, S. J., Frampton, M., Utell, M., Thilly, W. G., Waver, D. A., Ferencak, W. J., Jennings, C. A., Hammersley, J. R., Olson, D. A., and Willey, J. C. (2000), Normal bronchial epithelial cell expression of the glutathione transferase P1, Glutathione transferase M3, and Glutathione peroxidase is low in subjects with bronchogenic carcinoma, Cancer Research, 60, 1609-1618.)

Uniplex-StaRT-PCR

StaRT-PCR was performed using previously published protocols (Willey, J. C., Crawford, E. L., Jackson, C. M., Weaver, D. A., Hoban, J. C., Khuder, S. A., DeMuth, J. P. (1998), Expression measurement of many genes simultaneously by quantitative RT-PCR using standardized mixtures of competitive templates, Am. J. Respir. Cell Mol. Biol., 19, 6-17. DeMuth, J. P., Jackson, C. M., Weaver, D. A., Crawford, E. L., Durzinsky, D. S., Durham, S. J., Zaher, A., Phillips, E. R., Khuder, S. A., Willey, J. C., (1998), The gene expression index of c-myc×E2F-1/p21 is highly predictive of malignant phenotype in human bronchial epithelial cells, Am. J. Respir. Cell Mol. Biol., 19, 18-24. Crawford, E. L., Khuder, S. A., Durham, S. J., Frampton, M., Utell, M., Thilly, W. G., Weaver, D. A., Ferencak, W. J., Jennings, C. A., Hammersley, J. R., Olson, D. A., Willey, J. C., (2000), Normal bronchial epithelial cell expression of the glutathione transferase P1, Glutathione transferse M3, and Glutathione peroxidase is low in subjects with bronchogenic carcinoma, Cancer Research, 60, 1609-1618. Crawford, E. L., Godfridus, J. P., Noordhuis, P., Rots, M. G., Vondracek, M., Grafstrom, R. C., Lieuallen, K., Lennon, G., Zahorchak, R. J., Georgeson, M. J., Wali, A., Lechner, J. F., Fan, P-S., Kahaleh, B., Khuder, S. A., Warner, K A., Weaver, D. A., Willey, J. C., (2001), Reproducible gene expression measurement among multiple laboratories obtained in a blinded study using standardized RT (StaRT)-PCR, submitted. Gene Express System 1 Instruction Manual, Gene Express National Enterprises, Inc. (2000), www.genexnat.com.) with G.E.N.E. system I expression kit (Gene Express National Enterprises, Inc.).

There were six CT mixtures A-F and appropriate primers included in System 1 kit. The concentration of "target gene" CTs varies in each mix compared to the concentration of the "reference gene" actin. The master mix contained Rnase-free water, $MgCl_2$ buffer, dNTPs, cDNA, CT mixture from G.E.N.E. system I kit and taq polymerase. The master mix was placed into tubes containing individual gene primers, and cycled in a Rapidcycler (Idaho Technology, Inc., Idaho Falls, Id.). The denaturing temperature was 94° C., annealing temperature was 58° C. and elongation temperature was 72° C. for each cycle. After amplification, each pcr product was analyzed by capillary electrophoresis on an Agilent 2100 Bioanalyzer machine. The area under the curve of each native template (NT) was compared to that of its respected competitive template (CT) to determined gene expression values. The unit for each expression value was molecules per $10^6$ β-actin molecules.

Acquisition of Bronchogenic Carcinoma Samples

Fine needle aspirate (FNA) of primary lung cancer were obtained from patients at the Medical College of Ohio. An informed, signed consent was obtained from patients according to NIH and institutional guidelines prior to each procedure. Most cells were placed directly on slides for diagnostic purposes. Cells not needed for diagnostic purposes were collected in Preservcyt® Solution (CYTYC/Boxborough, Mass.). After final cytopathologic diagnosis, remaining cells in Preservcyt were pelleted in our laboratory and RNA was extracted. Cell number and viability were evaluated on cells through analysis of cells on glass slides.

Results

In an effort to determine optimal collection and preservation of RNA in FNA specimens, H1155 cells (NSCLC) were placed in 3 storage reagents, RNA Later, Preservcyt and Tri Reagent. To determine effects of time and temperature on RNA, H1155 cells were kept at 4° C. or −20° C. for 1, 3, 10 and 30 days.

High quality RNA, indicated as ++ (exhibited the presence of 18s and 28s ribosomal bands) was detected in H1155 NSCLC cells stored in each reagent up to 10 days (Table 6). RNA was preserved equally well in Preservcyt and TRI reagent after 30 day storage. RNA was partially degraded after 30 day storage in RNA Later (+−) at 4° C. and was not preserved at −20° C.

To determine if RNA was suitable for StaRT-PCR, it was reverse transcribed and β-actin expression was evaluated. β-actin was detected in all samples exhibiting high quality or partially degraded RNA (FIG. 6—Table 6). As expected, β-actin was not detected in cells stored in RNA later for 30 days at −20° C. RNA quality correlated highly with the ability to be pcr amplied. Optimal storage reagents for short term storage (1-10 days) are Preservcyt and RNA later and for long term storage, greater than 10 days Preservcyt is recommended. Preservcyt is also advantageous to use at institutions that utilize the Thin Prep System for cytological analysis.

After determination of optimal collection and storage conditions, lung FNA specimens were placed in Preservcyt and stored at 4° C. Similar to the H1155 cells, RNA quality was evaluated in 9 of 10 FNA specimens (FIG. 7—Table 7). Five samples had high quality (++) or partially degrated (+−) RNA. As expected, all five samples were pcr amplifiable and β-actin was detected. On sample was not evaluated (NE) prior to reverse transcription and 4 samples exhibited poor quality RNA(−). β-actin was detected in the NE specimen and unexpectedly was detected in 2 of the RNA (−−) samples. When high quality RNA is present, it is highly suitable for PCR experiments. When poor quality RNA is present, it less likely to be pcr amplifiable but still may be useful.

In an attempt to determine why 4 samples had poor quality RNA, the cytological characteristics were determined independently by a pathologist for each specimen. Cellularity, viability and percent tumor/normal cells were determined for each sample (Table 7). Seven of 10 samples had low cellularity (L) and low viability (L). Three of these samples had a (++) or (+−) RNA status and all were pcr amplifiable (+β-actin). Of the remaining four samples with low cellularity and low viability, two were pramplifiable and two were not. Three of 10 samples had intermediate (I) or high (H) cellularity and viability. All three had good quality RNA and were pcr amplifiable. It is likely that cellularity is related to the amount of RNA extracted and viability may be related RNA quality obtained from these cells. Specimens and intermediate to high cellularity are optimal for gene expression studies, but cells with low cellularity and low viability are still suitable, since 5 of 7 were pcr amplifiable.

In 7 of 10 samples, the % of tumor cells varied from 60-90%. Two samples had 20% tumor cells and one was 10% tumor cells. The FNA diagnosis, determined at time of same acquisition was NSCLC in 6 samples and atypical in 4. To confirm the presence of a malignant phenotype, 3 genes associated with malignancy, c-myc, E2F-1 and p21 were evaluated in 8 of 10 FNA's and the malignancy index of c-myc× E2F-1/p21 was determined (FIG. 8—Table 8). As expected, 5 of the +NSCLC samples had a very high index value that ranged from $1.0E^4$ to $3.6E^6$ (as molecules per $10^6$ β-actin molecules). Three of the four atypical samples also exhibited high malignant gene expression indices, with values ranging from $7.2E^3$-$5.0E^4$. After additional analysis, the three atypical samples that gene expression data was obtained from were later confirmed as small cell lung cancer (SCLC). The percentage of tumor cells in the atypical samples ranged from 20 to 80% indicating even a small number of abnormal cells were sufficient and detected by the gene expression index c-myc×E2F-1/p21.

While, FNA analysis of pulmonary nodules is a common diagnostic method, this is the first example to use a standardized, quantitative gene expression method on human lung FNA samples. Gene expression profiling of these small, non-renewable cell populations have diagnostic and prognostic implications and lead to individualized patient care. Different gene expression patterns are useful to discriminate between SCLC and NSCLC, and earlier identification of a malignant phenotype will optimize clinical treatment. In addition, StaRT-PCR is also useful to identify gene expression patterns and associate them with clinically relevant phenotypes, e.g. chemosensitivity and metastatic potential to improve patient prognosis.

In this example, 5 of the FNA samples initially diagnosed as NSCLC, and later confirmed to be NSCLC had high index values. The range of expression for these +NSCLC specimens were $1.0E^4$-$3.6E^6$. In this sample set, 4 were 90.0% tumor cells and sample #172 had only 20% tumor cells, yet had the highest index value, $6.5E^5$. Three of the FNA samples, cytologically diagnosed as atypical, and later confirmed to be SCLC also had high index values. They ranged from $7.20E^3$-$5.0E^4$ mRNA molecules per $10^5$ molecules β-actin mRNA. The percentage of tumor cells in these samples ranged from 20-80%.

Other Embodiments

The genes and IGEI marker sets described herein provide valuable information for the identification of new drug targets against NSCLC, and that information may be extended for use in the study of carcinogenesis in other tissues. These sequences may be used in the methods of the invention or may be used to produce the probes and arrays of the invention.

The present invention is not to be limited in scope by the specific embodiments described herein, but are intended as single illustrations of individual aspects of the invention and it is to be understood that functionally equivalent methods and components are within the scope of the invention, in addition to those shown and described herein and will become apparent to those skilled in the art from the foregoing description and accompanying drawings. Such modifications are intended to fall within the scope of the appended claims.

All references cited herein, including journal articles, patents, and databases are expressly incorporated by reference.

We claim:

1. A method for selecting a treatment for non-small cell carcinoma (NSCLC), the method comprising the steps of:
   a) providing a sample of NSCLC cells from an individual;
   b) determining the levels of mRNA of each of ERCC2, XPC, ABCC5, GTF2H2, XPA and XRCC1 in the sample of NSCLC cells, wherein the levels are determined by quantitative RT-PCR;
   c) calculating ratios of ABCC5/GTF2H2, XPA/XPC, XRCC1/XPC, ERCC2/XPC and ERCC2/GTF2H2 using the levels determined in step b);
   d) comparing the ratios of step c) to that of ratios of ABCC5/GTF2H2, XPA/XPC, XRCC1/XPC, ERCC2/XPC and ERCC2/GTF2H2 in control NSCLC cells that are cisplatin-resistant, wherein comparing the ratios of step c) to those in control NSCLC cells comprises determining an $R^2$ value for each ratio;
   e) identifying the sample of NSCLC cells as being cisplatin-resistant based on the comparison of the ratios in step d), wherein the sample of NSCLC cells are identified as being cisplatin resistant when the $R^2$ value determined in step d) for each ratio is about 0.87 or greater; and
   f) selecting a treatment for NSCLC, wherein treatment not involving cisplatin is selected when the sample of NSCLC cells are identified as being cisplatin resistant in step e) and treatment involving cisplatin is selected when the $R^2$ value determined in step d) for any ratio is less than 0.87.

2. A method of treating an NSCLC cancer patient, the method comprising:
   a) obtaining two or more samples comprising NSCLC cancer cells from the NSCLC cancer patient during a course of treatment with cisplatin;
   b) for each sample, assaying the sample of NSCLC cells to determine the levels of mRNA of each of ERCC2, XPC, ABCC5, GTF2H2, XPA and XRCC1, wherein the levels are determined by quantitative RT-PCR;
   c) for each sample, calculating ratios of ABCC5/GTF2H2, XPA/XPC, XRCC1/XPC, ERCC2/XPC and ERCC2/GTF2H2 using the levels determined in step b);
   d) for each sample, comparing the ratios of step c) from the sample of NSCLC cells to ABCC5/GTF2H2, XPA/XPC, XRCC1/XPC, ERCC2/XPC and ERCC2/GTF2H2 ratios of control NSCLC cells that are cisplatin-resistant, wherein comparing the ratios of step c) to those in control NSCLC cells comprises determining an $R^2$ value for each ratio;
   e) for each sample, identifying the sample of NSCLC cells as being cisplatin-sensitive based on the comparison of the ABCC5/GTF2H2, XPA/XPC, XRCC1/XPC, ERCC2/XPC and ERCC2/GTF2H2 ratios of each sample to the ABCC5/GTF2H2, XPA/XPC, XRCC1/XPC, ERCC2/XPC and ERCC2/GTF2H2 ratios of the control NSCLC cisplatin-resistant cells, wherein the sample of NSCLC cells are identified as being cisplatin sensitive when the $R^2$ value determined in step d) for any ratio in a sample is less than 0.87; and
   f) continuing cisplatin treatment for the NSCLC cancer patient when the NSCLC cells of the samples maintain cisplatin sensitivity as identified by in step e) during the course of cisplatin treatment.

3. The method of claim 1, wherein step a) includes: obtaining mRNA from the sample, wherein the mRNA comprises ERCC2, XPC, ABCC5, GTF2H2, XPA and XRCC2 mRNA.

4. The method of claim 3, wherein the sample is taken from the individual before cisplatin chemotherapy is administered to the individual.

5. A method to assess response to cisplatin treatment of non-small cell carcinoma (NSCLC) in a human subject having NSCLC comprising:
   a) determining the levels of mRNA of each of ERCC2, XPC, ABCC5, GTF2H2, XPA and XRCC1 in a sample of NSCLC cells from the subject before a cisplatin treatment is administered to the subject, wherein the levels of mRNA are determined by quantitative RT-PCR;
   b) calculating ratios of ABCC5/GTF2H2, XPA/XPC, XRCC1/XPC, ERCC2/XPC and ERCC2/GTF2H2 for the sample of NSCLC cells from the subject before a cisplatin treatment is administered to the subject using the levels determined in step a);

c) determining the levels of mRNA of each of ERCC2, XPC, ABCC5, GTF2H2, XPA and XRCC1 in a sample of NSCLC cells from the subject after a cisplatin treatment has been administered to the subject, wherein the levels of mRNA are determined by quantitative RT-PCR;

d) calculating ratios of ABCC5/GTF2H2, XPA/XPC, XRCC1/XPC, ERCC2/XPC and ERCC2/GTF2H2 for the sample of NSCLC cells from the subject after a cisplatin treatment has been administered to the subject using the levels determined in step c);

e) for each sample, comparing the calculated ratios for each sample to ABCC5/GTF2H2, XPA/XPC, XRCC1/XPC, ERCC2/XPC and ERCC2/GTF2H2 ratios of control NSCLC cells that are cisplatin-resistant, wherein comparing the calculated ratios for each sample to those in NSCLC cells comprises determining an $R^2$ value for each ratio; and f) predicting that the subject will respond to the cisplatin treatment when the $R^2$ values determined in step e) are less than about 0.87 in the sample of NSCLC cells from the subject before a cisplatin treatment is administered to the subject and the sample of NSCLC cells from the subject after a cisplatin treatment has been administered to the subject.

* * * * *

SEQUENCE LISTING

```
<160> NUMBER OF SEQ ID NOS: 48

<210> SEQ ID NO 1
<211> LENGTH: 21
<212> TYPE: DNA
<213> ORGANISM: Homo sapiens

<400> SEQUENCE: 1
gattcctatg tgggcgacga g                                              21

<210> SEQ ID NO 2
<211> LENGTH: 21
<212> TYPE: DNA
<213> ORGANISM: Homo sapiens

<400> SEQUENCE: 2
gattcctatg tgggcgacga g                                              21

<210> SEQ ID NO 3
<211> LENGTH: 40
<212> TYPE: DNA
<213> ORGANISM: Homo sapiens

<400> SEQUENCE: 3
ccatctcttg ctcgaagtcc gccagccagg tccagacgca                          40

<210> SEQ ID NO 4
<211> LENGTH: 22
<212> TYPE: DNA
<213> ORGANISM: Homo sapiens

<400> SEQUENCE: 4
cacctgaagg acttcgtgtc ag                                             22

<210> SEQ ID NO 5
<211> LENGTH: 22
<212> TYPE: DNA
<213> ORGANISM: Homo sapiens

<400> SEQUENCE: 5
tggtttacca ggggtactga ct                                             22

<210> SEQ ID NO 6
<211> LENGTH: 44
<212> TYPE: DNA
<213> ORGANISM: Homo sapiens

<400> SEQUENCE: 6
```

```
tggtttacca ggggtactga ctttggccat gctgtagaaa agac            44

<210> SEQ ID NO 7
<211> LENGTH: 24
<212> TYPE: DNA
<213> ORGANISM: Homo sapiens

<400> SEQUENCE: 7
gaagcacctt gggaatatca gaaa                                  24

<210> SEQ ID NO 8
<211> LENGTH: 24
<212> TYPE: DNA
<213> ORGANISM: Homo sapiens

<400> SEQUENCE: 8
aggcacacca gttgtctttg tcca                                  24

<210> SEQ ID NO 9
<211> LENGTH: 48
<212> TYPE: DNA
<213> ORGANISM: Homo sapiens

<400> SEQUENCE: 9
aggcacacca gttgtctttg tccagtacct cttgtaaggc attccaca        48

<210> SEQ ID NO 10
<211> LENGTH: 24
<212> TYPE: DNA
<213> ORGANISM: Homo sapiens

<400> SEQUENCE: 10
catctcttat gctgtccagt taac                                  24

<210> SEQ ID NO 11
<211> LENGTH: 24
<212> TYPE: DNA
<213> ORGANISM: Homo sapiens

<400> SEQUENCE: 11
gctcttgagg aatgatagag agtt                                  24

<210> SEQ ID NO 12
<211> LENGTH: 47
<212> TYPE: DNA
<213> ORGANISM: Homo sapiens

<400> SEQUENCE: 12
gctcttgagg aatgatagag agttggccat ccccagcgag gacttcc         47

<210> SEQ ID NO 13
<211> LENGTH: 22
<212> TYPE: DNA
<213> ORGANISM: Homo sapiens
<220> FEATURE:
<221> NAME/KEY: misc_feature
<222> LOCATION: (6)..(6)
<223> OTHER INFORMATION: "n" can be any of these four bases: A, G, C,
      or T

<400> SEQUENCE: 13
ggaatnggtg aactgggtga ag                                    22

<210> SEQ ID NO 14
```

```
<211> LENGTH: 22
<212> TYPE: DNA
<213> ORGANISM: Homo sapiens

<400> SEQUENCE: 14
caaggagtga tttccaaaga gt                                              22

<210> SEQ ID NO 15
<211> LENGTH: 44
<212> TYPE: DNA
<213> ORGANISM: Homo sapiens

<400> SEQUENCE: 15
caaggagtga tttccaaaga gtcagccagc acctctgtat aggc                      44

<210> SEQ ID NO 16
<211> LENGTH: 22
<212> TYPE: DNA
<213> ORGANISM: Homo sapiens

<400> SEQUENCE: 16
agaatcaaaa atcttcacca ct                                              22

<210> SEQ ID NO 17
<211> LENGTH: 22
<212> TYPE: DNA
<213> ORGANISM: Homo sapiens

<400> SEQUENCE: 17
ctttcctttt gtctactcca ag                                              22

<210> SEQ ID NO 18
<211> LENGTH: 44
<212> TYPE: DNA
<213> ORGANISM: Homo sapiens

<400> SEQUENCE: 18
ctttcctttt gtctactcca agtcagtagc cacttctggg aaag                      44

<210> SEQ ID NO 19
<211> LENGTH: 19
<212> TYPE: DNA
<213> ORGANISM: Homo sapiens

<400> SEQUENCE: 19
ggccttcttc accagctac                                                  19

<210> SEQ ID NO 20
<211> LENGTH: 19
<212> TYPE: DNA
<213> ORGANISM: Homo sapiens

<400> SEQUENCE: 20
gtagtccgtc ttgcccctg                                                  19

<210> SEQ ID NO 21
<211> LENGTH: 38
<212> TYPE: DNA
<213> ORGANISM: Homo sapiens

<400> SEQUENCE: 21
gtagtccgtc ttgcccctgt ggaactggtc ccgcaggt                             38

<210> SEQ ID NO 22
```

```
<211> LENGTH: 20
<212> TYPE: DNA
<213> ORGANISM: Homo sapiens

<400> SEQUENCE: 22 tcggggtca ttgttcttcc                                           20

<210> SEQ ID NO 23
<211> LENGTH: 20
<212> TYPE: DNA
<213> ORGANISM: Homo sapiens

<400> SEQUENCE: 23
tcttggctgg tatggtgtgc                                          20

<210> SEQ ID NO 24
<211> LENGTH: 40
<212> TYPE: DNA
<213> ORGANISM: Homo sapiens

<400> SEQUENCE: 24
tcttggctgg tatggtgtgc aggtgctaat ggcaacggag                    40

<210> SEQ ID NO 25
<211> LENGTH: 28
<212> TYPE: DNA
<213> ORGANISM: Homo sapiens

<400> SEQUENCE: 25
ctctttcagc atggcgcatt tggatggc                                 28

<210> SEQ ID NO 26
<211> LENGTH: 28
<212> TYPE: DNA
<213> ORGANISM: Homo sapiens

<400> SEQUENCE: 26
ctttcaattc ccctgacat ccataaca                                  28

<210> SEQ ID NO 27
<211> LENGTH: 50
<212> TYPE: DNA
<213> ORGANISM: Homo sapiens

<400> SEQUENCE: 27
ctttcaattc ccctgacat ccataacagc agacaccaaa gtaagaccac           50

<210> SEQ ID NO 28
<211> LENGTH: 20
<212> TYPE: DNA
<213> ORGANISM: Homo sapiens

<400> SEQUENCE: 28
catgatcctg aagcagacgt                                          20

<210> SEQ ID NO 29
<211> LENGTH: 20
<212> TYPE: DNA
<213> ORGANISM: Homo sapiens

<400> SEQUENCE: 29
gtgtccagga tgaaggatgt                                          20

<210> SEQ ID NO 30
```

```
<211> LENGTH: 40
<212> TYPE: DNA
<213> ORGANISM: Homo sapiens

<400> SEQUENCE: 30
gtgtccagga tgaaggatgt cagtgttgtc ttcctgattc                40

<210> SEQ ID NO 31
<211> LENGTH: 40
<212> TYPE: DNA
<213> ORGANISM: Homo sapiens

<400> SEQUENCE: 31
gtgtccagga tgaaggatgt cagtgttgtc ttcctgattc                40

<210> SEQ ID NO 32
<211> LENGTH: 29
<212> TYPE: DNA
<213> ORGANISM: Homo sapiens

<400> SEQUENCE: 32
tgtcggactt cctttgcttc ttctaatgc                           29

<210> SEQ ID NO 33
<211> LENGTH: 53
<212> TYPE: DNA
<213> ORGANISM: Homo sapiens

<400> SEQUENCE: 33
tgtcggactt cctttgcttc ttctaatgct cttcttcaca ataaatttaa gag    53

<210> SEQ ID NO 34
<211> LENGTH: 21
<212> TYPE: DNA
<213> ORGANISM: Homo sapiens

<400> SEQUENCE: 34
ggctactccc atcccgtgac t                                   21

<210> SEQ ID NO 35
<211> LENGTH: 21
<212> TYPE: DNA
<213> ORGANISM: Homo sapiens

<400> SEQUENCE: 35 tttcccttttt ggtcttcttg g                                  21

<210> SEQ ID NO 36
<211> LENGTH: 42
<212> TYPE: DNA
<213> ORGANISM: Homo sapiens

<400> SEQUENCE: 36 tttcccttttt ggtcttcttg gtcccctcct cttcatcaga ag            42

<210> SEQ ID NO 37
<211> LENGTH: 20
<212> TYPE: DNA
<213> ORGANISM: Homo sapiens

<400> SEQUENCE: 37
cccctgaaga gaccaaagca                                     20

<210> SEQ ID NO 38
```

```
<211> LENGTH: 20
<212> TYPE: DNA
<213> ORGANISM: Homo sapiens

<400> SEQUENCE: 38
ccattgaagg ctgtgacgta                                              20

<210> SEQ ID NO 39
<211> LENGTH: 40
<212> TYPE: DNA
<213> ORGANISM: Homo sapiens

<400> SEQUENCE: 39
ccattgaagg ctgtgacgta tcagggactg gcagatcagg                        40

<210> SEQ ID NO 40
<211> LENGTH: 20
<212> TYPE: DNA
<213> ORGANISM: Homo sapiens

<400> SEQUENCE: 40
tacgcagcgc ctccctccac                                              20

<210> SEQ ID NO 41
<211> LENGTH: 20
<212> TYPE: DNA
<213> ORGANISM: Homo sapiens

<400> SEQUENCE: 41
ctgttctcgt cgtttccgca                                              20

<210> SEQ ID NO 42
<211> LENGTH: 40
<212> TYPE: DNA
<213> ORGANISM: Homo sapiens

<400> SEQUENCE: 42
ctgttctcgt cgtttccgca accttggggg ccttttcatt                        40

<210> SEQ ID NO 43
<211> LENGTH: 20
<212> TYPE: DNA
<213> ORGANISM: Homo sapiens

<400> SEQUENCE: 43
tgatacccca actccctcta                                              20

<210> SEQ ID NO 44
<211> LENGTH: 20
<212> TYPE: DNA
<213> ORGANISM: Homo sapiens

<400> SEQUENCE: 44
aaagcaggag ggaacagagc                                              20

<210> SEQ ID NO 45
<211> LENGTH: 37
<212> TYPE: DNA
<213> ORGANISM: Homo sapiens

<400> SEQUENCE: 45
aaagcaggag ggaacagagc actgcaggga ccacagg                           37

<210> SEQ ID NO 46
```

```
<211> LENGTH: 20
<212> TYPE: DNA
<213> ORGANISM: Homo sapiens

<400> SEQUENCE: 46
gctgtccctc cccttgtct                                                      20

<210> SEQ ID NO 47
<211> LENGTH: 20
<212> TYPE: DNA
<213> ORGANISM: Homo sapiens

<400> SEQUENCE: 47
tgttccgctg ctaatcaaag                                                     20

<210> SEQ ID NO 48
<211> LENGTH: 40
<212> TYPE: DNA
<213> ORGANISM: Homo sapiens

<400> SEQUENCE: 48
tgttccgctg ctaatcaaag tactccccca tcatataccc                               40
```